US008698888B2

(12) United States Patent
Bonnet

(10) Patent No.: US 8,698,888 B2
(45) Date of Patent: Apr. 15, 2014

(54) SYSTEMS AND METHODS FOR COMPREHENSIVE HUMAN MOVEMENT ANALYSIS

(75) Inventor: Kenneth A. Bonnet, Riverside, CT (US)

(73) Assignee: Medical Motion, LLC, Riverside, CT (US)

( * ) Notice: Subject to any disclaimer, the term of this patent is extended or adjusted under 35 U.S.C. 154(b) by 556 days.

(21) Appl. No.: 12/914,951

(22) Filed: Oct. 28, 2010

(65) Prior Publication Data

US 2011/0102568 A1 May 5, 2011

Related U.S. Application Data

(60) Provisional application No. 61/256,930, filed on Oct. 30, 2009.

(51) Int. Cl.
*H04N 9/47* (2006.01)
*H04N 7/18* (2006.01)
(52) U.S. Cl.
USPC .......................................................... 348/77
(58) Field of Classification Search
USPC .................................... 348/77, 128, 135, 143
See application file for complete search history.

(56) References Cited

U.S. PATENT DOCUMENTS

| | | | |
|---|---|---|---|
| 6,056,671 A | 5/2000 | Marmer | |
| RE40,427 E | 7/2008 | Nashner | |
| 7,421,101 B2 | 9/2008 | Georgescu et al. | |
| 7,447,337 B2 | 11/2008 | Zhang et al. | |
| 7,492,268 B2 | 2/2009 | Ferguson et al. | |
| 7,532,744 B2 | 5/2009 | Sharoni et al. | |
| 7,591,793 B2 | 9/2009 | Orito et al. | |
| 7,664,317 B1 | 2/2010 | Sowerby | |
| 7,756,293 B2 | 7/2010 | Kuwabara et al. | |
| 7,782,358 B2 | 8/2010 | Nieminen et al. | |
| 2003/0228033 A1* | 12/2003 | Daniel et al. ................... | 382/104 |
| 2004/0002636 A1 | 1/2004 | Martin et al. | |
| 2007/0250286 A1 | 10/2007 | Duncan et al. | |
| 2007/0275830 A1 | 11/2007 | Lee et al. | |
| 2008/0100438 A1* | 5/2008 | Marrion et al. ................ | 340/555 |
| 2008/0122926 A1* | 5/2008 | Zhou et al. ..................... | 348/143 |
| 2008/0144887 A1 | 6/2008 | Sharoni et al. | |

(Continued)

FOREIGN PATENT DOCUMENTS

WO 2007020568 2/2007

OTHER PUBLICATIONS

Chang, R. et al., "An automated form of video image analysis applied to classification of movement disorders," Disability and Rehabilitation, 2000, vol. 22, No. 1/2, pp. 97-108.

(Continued)

*Primary Examiner* — Andy S. Rao
*Assistant Examiner* — Jared Walker
(74) *Attorney, Agent, or Firm* — Sheppard Mullin Richter & Hampton LLP

(57) ABSTRACT

A method, system, and computer-readable medium receive module configuration settings to configure a customized human movement examination module for a human movement examination item. A patient is instructed with audio instructions associated with the customized human movement examination module. A single camera is controlled having progressive scan capabilities according to the module configuration settings to allow recording of a performance by the patient of the human movement examination item. The recorded data is analyzed based on the information provided by the single camera to measure human movement exhibited by the patient.

18 Claims, 19 Drawing Sheets

(56) References Cited

U.S. PATENT DOCUMENTS

| | | |
|---|---|---|
| 2008/0166020 A1 | 7/2008 | Kosaka et al. |
| 2008/0219502 A1 | 9/2008 | Shamaie |
| 2008/0306412 A1 | 12/2008 | Nieminen et al. |
| 2009/0087096 A1 | 4/2009 | Eaton et al. |
| 2009/0125223 A1 | 5/2009 | Higgins |
| 2010/0098165 A1 | 4/2010 | Farfade et al. |
| 2010/0177933 A1* | 7/2010 | Willmann et al. ............ 382/107 |
| 2010/0189410 A1 | 7/2010 | Jain et al. |

OTHER PUBLICATIONS

Cho, Chien-Wen et al., "A vision-based analysis systems for gait recognition in patients with Parkinson's disease," Expert Systems with Applications, vol. 36, 2009, pp. 7033-7039.

Das, Resul, "A comparison of multiple classification methods for diagnosis of Parkinson disease," Expert Systems with Applications, 2010, vol. 37, pp. 1568-1572.

Elble, Rodger et al., "Tremor amplitude is logarithmically related to 4- and 5- point tremor rating scales," Brain, 2006, vol. 129, pp. 2660-2666.

Fahn, S. et al., "Unified Parkinson's Disease Rating Scale," In: Fahn S, Marsden CD, Calne DB, Goldstein M, eds. Recent Developments in Parkinson's Disease. Florham Park, NJ: Macmillan, 1987, 153-163.

Fahn, S. et al., "Unified Parkinson's Disease Data Form," In: Fahn S, Marsden CD, Calne DB, Goldstein M, eds. Recent Developments in Parkinson's Disease. Florham Park, NJ: Macmillan, 1987, 2 pages.

Gao, X.K. et al., "Parkinson Movement Tests Performance: Feasibility and Reliability of Video Feature Extraction for Quantization of Standard Test Movements," AAN, Toronto, Apr. 2010.

Gao, X.K. et al., "Parkinson Movement Tests Performance: Effects of Acute Medication Challenge on Quantitative Measures in Standard Movement Tests," AAN, Toronto, Apr. 2010.

Goetz, C.G., "Movement Disorder Society Unified Parkinson's Disease Rating Scale (MDS-UPDRS)," Jul. 2008, 31 pages.

Goetz, C.G., "Movement Disorder Society Unified Parkinson's Disease Rating Scale (MDS-UPDRS): a new scale for the evaluation of Parkinson's . disease," Revue Neurologique, 2009, pp. 1-4.

Green, Richard et al., "Quantifying and Recognizing Human Movement Patterns From Monocular Video Images—Part I: A New Framework for Modeling Human Motion," IEEE Transactions on Circuits and Systems for Video Technology, 2004, vol. 14(1), 179-190.

Green, Richard et al., "Quantifying and Recognizing Human Movement Patterns from Monocular Video Images—Part II: Applications to Biometrics," IEEE Transactions on Circuits and Systems for Video Technology, 2003, vol. 14, pp. 179-190.

Green, Richard et al., "Video Analysis of Gait for Diagnosing Movement Disorders," Journal of Electronic Imaging, 2000, vol. 9(1), pp. 16-21.

International Patent Application No. PCT/US2010/054821, International Search Report and Written Opinion mailed Jun. 27, 2011.

Lee, Howard et al., "Video Analysis of Human Gait and Posture to Determine Neurological Disorders," Journal on Image and Video Processing 2008 Article ID 380867, pp. 1-12.

Louis, Elan et al., "Diagnosing Parkinson's Disease Using Videotaped Neurological Examinations: Validity and Factors that Contribute to Incorrect Diagnoses," Movement Disorders, 2002, vol. 17(2), pp. 513-517.

Marsden, C.D. et al., "Assessment of Extrapyramidal Disorders," Brit. J. Clin. Pharmacol, 1981, vol. 11, pp. 129-151.

Morris, Meg E., "Movement Disorders in People with Parkinson Disease: A Model for Physical Therapy," Physical Therapy, 2000, vol. 80(6), pp. 578-597.

Tavares, João Manuel R.S. et al., "Computer Analysis of Objects' Movements in Image Sequences: Methods and Applications," National Conference on Multibody System Dynamics, Portugal, Dec. 6-7, 2007, 8 pages.

Vasconcelos, Maria João M. et al., "Human motion analysis: Methodologies and Applications," Proc. Intel Symposium CMBBE, 2008, pp. 1-6.

* cited by examiner

SYSTEMS AND METHODS FOR COMPREHENSIVE HUMAN MOVEMENT ANALYSIS

CROSS-REFERENCE TO RELATED APPLICATIONS

The present application claims the benefit of Provisional U.S. Application Ser. No. 61/256,930, filed Oct. 30, 2009 and entitled "Systems and Methods for Comprehensive Human Movement Analysis", the disclosure of which is incorporated herein by reference.

BACKGROUND

The examination and analysis of human movement has been a longstanding tradition in the field of neurology. Doctors analyze human movement in order to diagnose and treat health problems such as, for example, Parkinson Disease, Hungtington Disease, Tourette Syndrome, tardive dyskinesia, dystonias, tremor disorders, stroke-related movement limitation, consequences of stroke, peripheal neuromuscular injury, demyelinating diseases, tic disorders, restless leg syndrome, motor overflow disorders, cerebral palsy, and any compromise that is reflected in altered human movement.

SUMMARY

Systems, methods, and computer readable media for comprehensive human movement analysis are described herein. Some embodiments are summarized in this section In one embodiment, provided is a method and a computer-readable medium having stored thereon a set of instructions, which when executed by a computer, perform a method, including: receiving module configuration settings to configure a customized human movement examination module for a human movement examination item; instructing a patient with audio instructions associated with the customized human movement examination module; controlling a single camera having progressive scan capabilities according to the module configuration settings to allow recording of a performance by the patient of the human movement examination item; and analyzing the recorded data based on the information provided by the single camera to measure human movement exhibited by the patient.

In one embodiment, the module configuration settings include at least one from a group consisting of camera zoom, camera focus, camera orientation, camera pan, camera frame rate, camera tilt, camera brightness, camera iris, camera gain, camera white balance blue, camera white balance red, and camera exposure.

In one embodiment, the module configuration settings may also include video and audio recording duration.

In one embodiment, further provided to the above method and computer-readable medium is synchronizing the audio instructions with a recording delay and a recording duration.

In one embodiment, in addition, the audio instructions include at least one from the group consisting of an instruction for the patient to take action according to the human movement examination item, an instruction to begin action, and an instruction to stop action.

In one embodiment, further provided to the above method and computer-readable medium is recording performance by the patient of the human movement examination item during the human movement examination module to generate the recorded data, wherein the recorded data comprises audio and video data.

In one embodiment, further provided to the analyzing step of the above method and computer-readable medium are: applying a human movement analysis module technique to the recorded data consistent with the customized human movement examination module; applying a tracking algorithm method to the recorded data consistent with the customized human movement examination module; producing summary result data as a by-product of the module analysis technique; and comparing the summary result data to normative standards for the customized human movement analysis module to determine whether the patient exhibits a human movement disorder.

In one embodiment, provided is a system including: a single camera having progressive scan capabilities; and a computing device coupled to the single camera, wherein the computing device is configured to: receive module configuration settings to configure a customized human movement examination module for a human movement examination item; instruct a patient with audio instructions associated with the customized human movement examination module; control the single camera according to the module configuration settings to allow recording of a performance by the patient of the human movement examination item; and analyze the recorded data based on information provided by the single camera to measure human movement exhibited by the patient.

The present disclosure includes methods and systems, including computer systems and data processing systems, which perform these methods. The present disclosure also includes computer readable media, which when executed on computer systems and data processing systems, cause the systems to perform these methods.

Many other features and embodiments of the present invention will be apparent from the accompanying drawings and from the following detailed description.

BRIEF DESCRIPTION OF THE DRAWINGS

The embodiments are illustrated by way of example and not limitation in the figures of the accompanying drawings in which like references indicate similar elements.

DETAILED DESCRIPTION

Figure 1A:
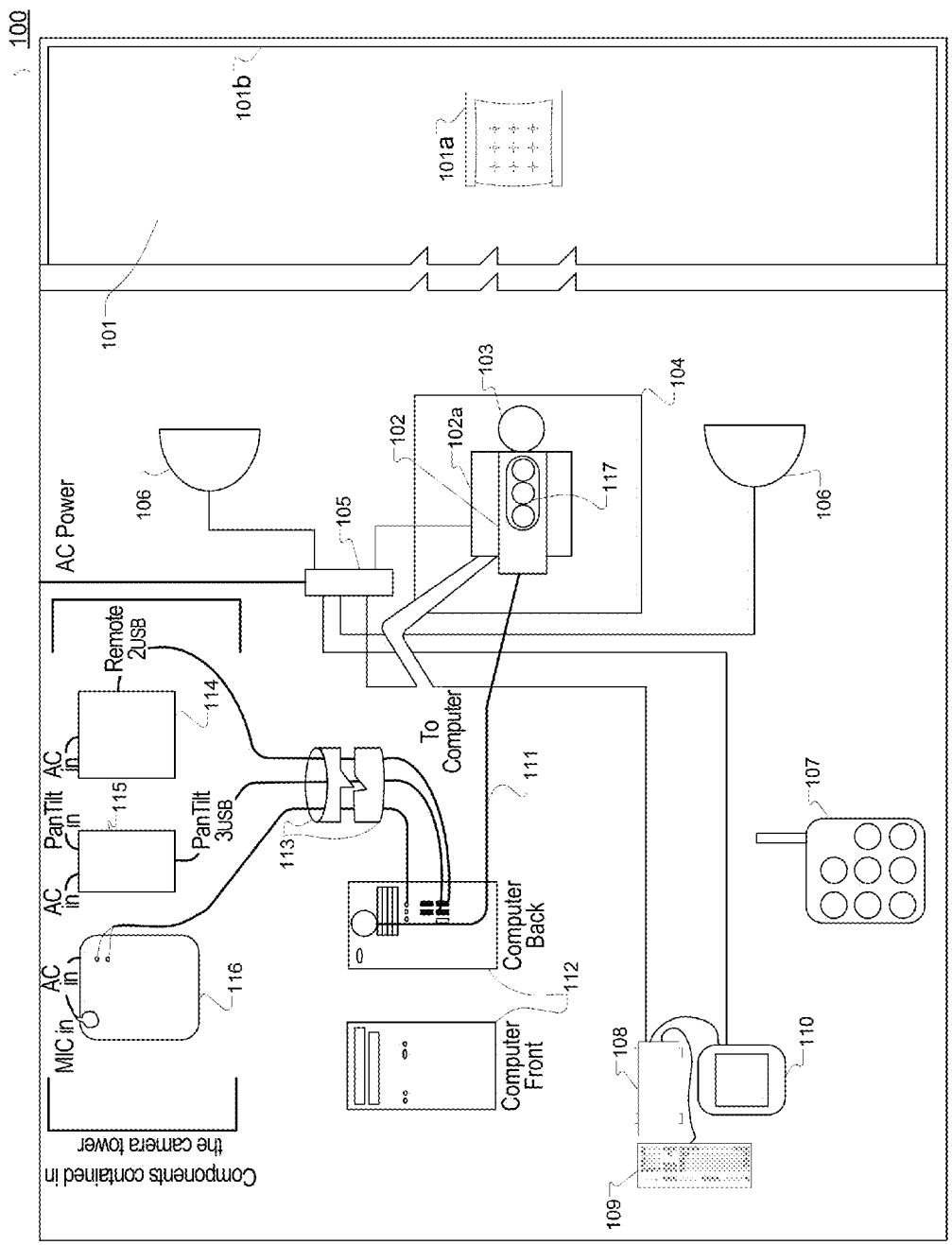
FIG. 1A shows a system for comprehensive human movement analysis according to one embodiment.

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment, and such references mean at least one.

The use of headings herein are merely provided for ease of reference and shall not be interpreted in any way to limit this disclosure or the following claims.

Reference in this specification to "one embodiment", "an embodiment", "the present disclosure", or the like, means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not other embodiments.

Rating scales such as the Unified Parkinson Disease Rating Scale (UPDRS), rating scales for ataxia, extrapyramidal movements, akathisia, Huntington's disease, childhood movement abnormalities, and the Hoehn and Yahr Scale exist as internationally-accepted clinical criteria for analyzing such human movement and contain human movement examination items such as examining hand tremors or the like. However, several studies have recently shown that when these rating scales are applied, their results yield significant degrees of variation, depending on a variety of factors such as the level of experience and training for a given physician. Thus, modern clinical movement analysis methods are largely limited to the visual observation by a physician, and are not approaches that utilize an objective and quantified framework. In one embodiment, the human movement analysis modules are designed to be flexible modules that can easily accommodate the addition or revision of any individual human movement examination item.

Three terms used throughout the present disclosure: (i) human movement examination item, (ii) human movement examination module, and (iii) human movement analysis module.

Human movement examination items are numerous, standard and common in the fields of neurology orthopedics, physical rehabilitation, and related fields. Human movement examination items usually focus on a specific movement from a patient—for example, "Finger-to-Nose" is an example of a human movement examination item.

In order to objectively and reliably administer these human movement examination items for patients, and to objectively record and measure the movement performance of a patient for an individual examination item, there may be timing, standardized audio instruction, camera settings and recording means that are coordinated with the automated administration of the human movement examination item to the patient This collection of settings is known as the human movement examination module, and is a compilation of, for example, camera settings, recording duration settings, delay settings, and standardized audio instructions and settings that are synchronous in time with the other settings.

Once recorded under the conditions that are rigorously and reliably produced by the human movement examination module, the video and audio recording has captured the performance of the human movement examination item by the patient. Then, a customized selection of analysis algorithms and heuristics is required to optimally extract the characteristics of that human movement item performance from the audio and video record. This collection of algorithms and heuristics is referred to as the human movement analysis module. The results produced by the human movement analysis module are then used to populate the appropriate points in a plot of the data, or in the appropriate points of a report format, and for comparison to norms.

An example of all three above-discussed terms in action is the Finger-to-Nose human movement examination item. The human movement examination module for the finger-to-nose human movement examination item includes camera settings, pan-tilt settings, timing delay settings, audio and video recording duration settings, and a customized audio instruction file synchronized with the settings associated with the finger-to-nose human movement examination item, and that instructs the patient to conform his or her movements for a specific human movement examination item. When performed, the performance of the finger-to-nose item is registered in audio-video file format. The analysis of that audio-video file format requires methods that are specific to the type of movement and relevant movement characteristics contained in that audio-video file format. That is where the human movement analysis module for the finger-to-nose item has a role, because the human movement analysis module includes methods, algorithms and heuristics that are specific to the type of movement recorded for the finger-to-nose examination item.

Therefore, a specific human movement examination item, performed during a specific human movement examination module with configuration settings (e.g., audio instructions, timings, camera settings) results in a recording file. The human movement analysis module is then applied, which serves as the specific analysis customized for that specific human movement examination module recording file recording the human movement examination item. The data in turn produced by the human movement analysis module then serves as the objectively measured characteristics of the patient performing the specific human movement examination item under the directions and audio instructions and timings and recordings of the specific human movement examination module.

In one embodiment, human movement examination items are items that may be from standardized movement examination instruments or standards, or that can be structured to examine a specific movement for clinical or research purposes. An example of an item is "Finger-to-Nose", a long-standing clinical examination item with standard parameters for instructions and for evaluation of movement related to visual-spatial target-error, or related to resting or intention tremor, or essential tremor that can be evident during the instructed movements.

In one embodiment, a human movement examination module may each include an audio instruction file, an associated set of camera settings (including, but not limited to pan-tilt settings, zoom settings, iris settings, white balance-blue and white balance-red settings, exposure settings, and gain settings), an associated software based set of elapsed time settings ("elapsed time settings" may be synonymous with the terms "delay timing" and "recording duration" used throughout the present disclosure) related to the audio instruction file, an associated set of signal lights pre-programmed into a sequence, an associated video and audio recording duration that is dependent upon the elapsed time settings related to the audio instruction file, and a specific positioning of the patient relative to the camera and to the camera settings such as pan-tilt settings, for example.

In one embodiment, a human movement analysis module may include algorithms, heuristics, and a sequence of software-based strategies or analyses used for the detection and quantification of movement that is applied to the recorded audio and recorded video sequence resulting from the execution of the software and settings during the human movement examination module. The collection of normative data produced from such a human movement analysis module and the module settings from the human movement examination module, and the comparison of the results from an individual recording resulting from the execution of a particular human movement examination module and settings relative to normative data collected for that same module may be performed with algorithms and analyses of a particular human movement analysis module for the purposes of, for example, producing a report with comparison values to show the result and its value relative to normative values.

In one embodiment, the addition of additional or alternative human movement examination modules, each with its own specific camera positioning, camera settings, patient positioning, audio instructions, audio instruction sound file (that may be as simple as a time-specific "Start" and "Stop" or the operator reading the instructions to the patient prior to the occurrence of "Start", etc.), and audio and video recording parameters may be performed. In one embodiment, the revision or addition of different human movement examination modules—each with its own specific camera positioning, camera settings (e.g., pan-tilt settings), patient positioning, audio instructions, and audio/video recording parameters may be performed. Therefore, the embodiments arising from the present disclosure are not limited to any particular movement disorders schedule, rating instrument, or convention. The present disclosure accommodates the design and embodiment of human movement examination modules involving camera positioning, camera settings, audio instruction module design, audio instruction timings, video and audio timing delays and parameters, video and audio recording for examination of motor performance, and vocal performance(s) that are independent of any published schedule or rating scale for movement disorders, but that can wholly accommodate the items contained in those specific clinical instruments without changing the embodiments of the present disclosure. The individual items within each of these specific clinical instruments may have been used individually for many years by clinicians in the field who do not use specific clinical instrument(s) or rating scales.

In one embodiment, the overall system of the present disclosure may serve as a "host system" that can embody almost any human movement examination item. The system may provide flexible lighting, flexible camera settings, flexible camera positioning, flexible frame rate for recording, flexible zoom, flexible audio recording, and flexible audio instruction and timing structures. The analysis provides, for example, spontaneous and tremor movement measurement, head movement measurement, finger and hand movement measurement, foot and heel movement measurement, vocal behavioral measurement, and walking and posture stability measurement. As such, the present disclosure can embody the test item or items of human movement examination items from any schedule, rating scale, or any human movement examination item newly constructed for human movement measurement. In one embodiment, the present disclosure may also be used for object movement, in addition to human movement, in a room environment with pre-defined patient or object positioning.

An exemplary human movement examination module is the module of finger-to-nose movement, which is accommodated as a human movement examination module in accordance with the present disclosure. The specific human movement examination item of finger-to-nose movement may not be specific to any particular examination standard, but can be constructed to accommodate a selected standard or combination of standards from, for example, a peer-reviewed publication or authoritative source. Therefore, the present disclosure may measure the clinically routine finger-to-nose movement examination item in a defined, repeatable and structured setting automatically with resulting objective and quantitative data. Several of the clinical examination movement items associated with the present disclosure provide novel and innovative automated, standardized and structured movement examination modules that now have been established and used for effective human movement analysis in this present disclosure.

The use of video systems currently available in some hospitals and other settings for clinical and quantitative human movement examination may utilize large and complex computer systems using multiple markers strategically placed on a patient, as well as multiple cameras. In one embodiment, the present disclosure is directed to a single camera system with pre-defined patient placement, and makes detailed systematic analysis available for in-office use by a technician, operator, researcher, physician, movement disorders laboratory employee or group or physical rehabilitation laboratory employee or group, or other similar person or entity, all the above hereinafter referred to as an "operator". In one embodiment, all the examination modules discussed below are incorporated into a single coherent system. In one embodiment, the present disclosure may be used with offices or examination rooms 22×13 feet or larger. In one embodiment, the present disclosure may be used in a space as small as 7×14 feet and can still accommodate most of the clinical human movement examination items that have been part of standard clinical practice for years.

In one embodiment, the timing and spatial arrangements for optimal movement examination may be aided by audio-video recording and the recordings may be used in software-based analysis. In one embodiment, the audio-video recordings may be automated.

In one embodiment, a comprehensive human movement analysis system is provided that achieves the objective and quantitative analysis of human movement and movement in general. A recording system records the data of human movement and an analysis system in turn analyzes that data according to a plurality of different human movement analysis modules. The human movement analysis modules employ algorithms and heuristics to analyze the video-recorded human movement data. Human movement of pre-defined types and human movement disorders in individuals exhibiting those movement types can be objectively and quantitatively measured, which in turn permits more accurate determination(s) of disorder subtype, tracking of treatment effects, tracking of disorder progression, and quantification of selective symptoms. In one embodiment, vocal latency, vocal pressure, articulation, and response content may also be measured in order to test for the presence of human movement disorders in patients. In one embodiment, a microphone device and audio mixer equalizer used in the system may allow the standardized recording of patient sounds. The sounds of the instructions may also be delivered to the patient prior to or during the recording phase of each examination module. Audio instructions may consist in the recording phase, for example, of simply "Start" and "Stop" at specific time points in the audio instruction sound file to signal when the patient is to perform a human movement examination item instructed by the system via pre-recorded audio instructions. In this manner, the standard clinical questions asked by the audio instruction presentation for specific examination modules may allow subsequent analysis to determine the latency for the patient to respond, the vocal pressure of the response, the articulation of the response, and the word content of the response, since the presentation and duration of each clinical question may be presented in a standardized manner and a reliably repeatable manner. In one embodiment, analysis software permits the analysis of vocal latency (time of delay after completion of the automated question presentation) to respond, and analysis of the sound pressure (reflecting amplitude) of patient answers in a manner that permits comparison to the same response of vocal latency and sound pressure in control subjects studied in same or similar conditions.

In one embodiment, a system is provided that achieves the objective and quantitative analysis of human movement and movement in general. In one embodiment, methods and algorithms and heuristics process data (that exist as either numbers or in graphical/video form) and produce, as end results, either plots or form reports.

A unique method and algorithm known as the Summation of the Absolute Value of Laplace transforms across all three Color Planes (SALCP), wherein absolute values need not always be used, but arithmetic values can be used as well, is an advanced and sophisticated method and algorithm that analyzes frames within video data to determine movement, and has wide-ranging applications beyond just human movement analysis.

Overall System

FIG. 1A shows a system for comprehensive human movement analysis according to one embodiment. Human movement analysis system 100 includes a variety of components. Subject area 101 includes a chair 101a and video wall 101b, which may include at least one muslin video wall of a specific blend of colors, shown in FIG. 1A as three muslin video walls that completely flank the chair 101a. A test subject, usually a human being, but which can be any object, animal or machine that can or cannot move, may sit in the chair 101a or in the position normally occupied in the field of view by the chair 101a to be recorded. In one embodiment, chair 101a can be of a low back variety, padded with arms, and/or equipped with removable elbow cups, one on each arm of the chair 101a; it is beneficial to be able to make the chair 101a comfortable for a subject/object to sit in. In one embodiment, a chair 101a need not be used; the subject or object can be standing up without a chair 101a, or another prop such as a stool or platform can be used. Video wall 101b may be made of muslin or other material. Muslin is a finely-woven, usually cotton-based fabric that is either dyed with a uniform color conducive to video environments or printed with a pattern. Muslin also absorbs rather than reflects light: as a result, light reflected off the subject is illuminated, making it easier to detect the subject's movement. The video wall 101b may be hung on a wall or walls, laid on a floor and/or ceiling as a background. In one embodiment, the video wall 101b may consist of a variegated combination of colors in an abstract pattern, resembling camouflage, in which the colors represent a range of color that is rather unlike the objects of interest that will be recorded, such as skin and human features. In one embodiment, the video wall 101b may be made from another material. In one embodiment, the video wall 101b may not be used. In one embodiment, the video wall 101b may be realized by selectively choosing minimally reflective paints for the wall, floor and ceiling surfaces of the room for human movement analysis system 100.

Camera 102, which can have a microphone 103, can be placed on a tower 104. Camera 102 may also have a pan-tilt unit 102a to control panning (horizontal movement) and tilting (vertical movement) of the camera 102. The camera 102 is used to record the subject or object, which can sit on the chair 101a as shown in FIG. 1A, or can be standing or in any other pose. In one embodiment, the camera 102 does not record but feeds live video frames to the computer storage 108 of the computer 112 for subsequent storage and analysis. In one embodiment, camera 102 may accommodate, for example, Gigawire, USB, Zigbee, Firewire (1394a and 1394b and subsequent 1394-based conventions) and wireless camera communication (e.g., IEEE 802.11) for input or communicative coupling to a computer. In one embodiment, the camera 102 can be a progressive-scan, motorized zoom camera with solid state image registration technology that permits computer-controlled settings of gamma, red-white balance, blue-white balance, brightness, exposure, iris, gain, and focus before the start of video recording. In one embodiment, a non-zoom lens video camera may be used. In one embodiment, an interlaced camera may be used. In one embodiment, a DFK 31BF03.Z from "The Imaging Source" may be used as camera 102, which is a firewire video color camera, and can be equipped with an IC Capture Software Suite. The microphone 103 can also be separate from the camera 102. In the case of the DFK 31BF03.Z model camera, the microphone 103 may be separate. In one embodiment, the pan-tilt unit 102a and the camera 102 may be separate entities. In one embodiment, the pan-tilt unit 102a and the camera 102 may be the same entity or attached to one another. In one embodiment, other 60 fps zoom cameras may be used for camera 102.

With any video camera 102, if the video stream or audio-video stream is directed through a computer storage 108 for storage or for recording, the computer may contain image capture software. In one embodiment, the digital image capture software may read input video stream data from the camera 102 and output individual frames to storage media at a rate that accommodates frame rates. In one embodiment, frame rates can be from less than one frame per second to more than 2000 frames per second, based upon camera and video storage capacity and speed capabilities. In one embodiment, the range to be used may span from 30 fps to 60 fps.

In one embodiment, the microphone 103 can be part of the camera 102 assembly. In one embodiment, the microphone 103 can be separate and connected to the computer storage 108 through an audio mixer equalizer 116. In the case of any video camera, the camera 102 may also contain a video and audio recording unit, or the camera 102 and microphone 103 may be separate and independent entities. In one embodiment, overall host software, which may be located in the computer storage 108, may accommodate either situation, and in the latter situation of the camera 102 and microphone 103 being separate, the overall host software may write the audio into the output video file to produce a standard audio-video file format, and simultaneously a separate audio file that can be analyzed individually or from the audio-video file. In one embodiment, a minimum of a 640×480 pixel density with Bayer color detection convention resulting in deBayering to three color planes may be used, but lesser or greater pixel density may be used as well, which may provide smaller or larger video frame image matrices or provide 720×480 or 1024×768 or higher resolutions. In one embodiment, the digital image capture software may read input video stream data from the camera 102 and output individual frames of data in an appropriate format to computer storage 108 at a rate that accommodates frame rates for progressive scan images from lower than 15 fps to greater than 120 fps.

Lights 106 and additional ceiling lighting (not shown) can be used to illuminate subject area 101. In one embodiment, lights 106 may include adjustable light stands of three bulb capacity, holding at least two compact fluorescent 32 Watt bulbs that may be at 2700K each. In one embodiment, ceiling lighting positioned above the subject area 101 may include ceiling, 36", four-tube fluorescent lights that may be at 4200K. In one embodiment, 4200K ceiling fluorescent lights may be used along with using the four 2700K lights as "spots" to highlight specific body parts. In one embodiment, adequate ceiling lighting may be used without the 2700K "spots". Proper and adequate lighting may be focused upon the subject in order to maximize the accuracy of the recording or measurement results. In one embodiment, fluorescent lighting is used to generate minimal heat so as to create a comfortable temperature environment for the patient.

Communications link 111 connects camera 102 to computer 112. Communications link 111 may include, for example, 1394a or 1394b Firewire, USB, Gigawire, IEEE 802.11, 802.xx or other communication standards or protocols. Computer 112 can control the camera 102 via the communication link 111. In one embodiment, computer 112 can control the pan-tilt settings 142 and camera settings 140 (140 and 142 are shown in FIG. 1D) of the camera 102 via a pan-tilt controller 115, which controls the pan-tilt unit 102 of the camera 102. In one embodiment, the audio mixer equalizer 116 may be a passive component where an operator controls by hand gain, balance and tone settings that remain fixed throughout a recording session. In one embodiment, the audio mixer equalizer 116 is computer-controlled and may have settings that are also computer-controlled. Remote control receiver 114 receives signals from remote control unit 107 in order to control operations of the computer 112 and the camera 102 without the operator having to be at the computer 112 or camera 102. In one embodiment, the remote control unit 107 may be based upon radio frequency pulse code modulation (e.g., a different pulse code sequence is transmitted for up to 300 feet for each key of 8 that is pressed). In one embodiment, the remote control unit 107 may be controlled using wireless communications of infrared or other wireless communication protocols, such as Bluetooth, Zigbee, 900 MHz, etc. For example, for recording purposes, image capture and camera control and a video frame capture software suite can be installed in the computer 112 or the camera 102. In one embodiment, the camera 102 may have both camera control software and video frame capture software applications. In one embodiment, the computer 112 can be a multimedia desktop or similar computer having high drive data transfer rate speeds and drive speeds of at least, for example, 3 Gb/s for a data transfer rate, and high resolution graphics card processing capabilities to support visual, graphics-intense capacity on a 32-64 bit machine with an operating system comparable to Windows XP SP2 or Windows Vista or Windows 7 installed inside the computer 112. Connected to the computer 112 are also monitor 110 to display the contents of the programs and live video views. In one embodiment, monitor 110 may be a 24 inch computer display monitor. In one embodiment, the monitor 110 may be a combined computer-monitor unit in the same physical encasement enclosing computer 112, computer storage 108 and monitor 110. In one embodiment, keyboard 109 may also be coupled to computer 112, and may reside within or outside the computer 112.

In one embodiment, the computer 112 may be a computer system. In one embodiment, the computer 112 may be a plurality of computers or computer systems. In one embodiment, the computer 112 may be a network of computers or computer systems communicatively coupled together.

Signal light 117 may be located on top of the camera 102, and is in one embodiment a Delcom 907241 signal light. In one embodiment, signal light 117 is a three-light (red, yellow and green), USB-controlled signal light device. The signal light 117 can include three colors to indicate the operation currently being performed by the computer 112 and to describe to the operator the current sequential operation of the computer 112 so that the operator can choose not to stay near the keyboard 109/computer 112 in order to constantly view the monitor 110 in order to see the current phase of operation of a module and to await the next command or event to proceed. In other words, the signal light 117 essentially tells the operator what the computer 112 is doing without the operator having to go to the monitor 110 of the computer 112 and see for himself or herself. Merely as an example, and as shown in FIG. 1A, red in the signal light 117 may mean that the computer programs have completed their processing and are ready to proceed to the next module, yellow may mean that the computer 112 is setting up the next selected module to execute, and green may mean that the process is currently being executed. In one embodiment, the signal light 117 is not limited to those three colors and the red, green and yellow example has been provided as merely an example. In one embodiment, another signal light 117 may be located anywhere in the room that provides an unimpeded view by the operator without distraction of the patient or object being recorded. In one embodiment, the computer storage 108 may contain software that selects a specifically colored light from the signal light 117 at a specific phase of the sequence of operating the phases of a module when recording the movement or performance of a patient or object. In one embodiment, the signal light 117 can appear elsewhere or anywhere in the room or on any object.

The audio mixer equalizer 116 includes MIC in and AC power-in connectors and Audio Out output connectors in order to control the audio recording parameters from the microphone 103, attached to the camera 102, or separate from the camera 102, and the recording environment in general. Audio mixer equalizer 116 may be in one embodiment a Behringer Xenix 702 Sound Mixer and microphone 103 may be in one embodiment a Behringer Pro B2 phantom dual diaphragm dynamic microphone and stand, equipped with a 50 foot three-conductor cable to accommodate placement of the microphone 103 and stand near the placement of the patient, with the audio mixer equalizer 116 in proximity of the computer 112 and camera 102 and camera tower 104. Pan-tilt controller 115 controls the pan-tilt unit 102a, which in turn controls the tilt (vertical) and pan (horizontal) positioning of camera 102. Pan-tilt controller 115 may be in one embodiment a DPerception PTU-46 pan-tilt unit with corresponding controller. In one embodiment, pan-tilt unit 102a may be mounted to the underside of the camera 102 and the top side of the tower 104, and then pan-tilt unit 102a may be connected by multi-conductor cables to the pan-tilt controller 115. The pan-tilt controller 115 in turn connects to a port in the computer 112 having computer storage 108 allowing computer reading of the position of the pan and tilt portions of the pan-tilt unit 102a, and also allowing the computer 112 to send pan and tilt settings to the pan-tilt controller 115.

Remote control receiver 114 receives numerically encoded signals from the remote control unit 107 in order to control operations in the computer 112 in the form of software interpreted commands. In one embodiment, the remote control receiver 114 may be a complementary receiver that receives the data from whichever button is pressed in the remote control unit 107, which then interprets the signal and sends the result to the computer 112 by USB cable. In one embodiment, remote control unit 107 may be a battery-powered, 8-button, miniature radiofrequency radio-control unit with a range of approximately 300 feet, and the receiver may be in one embodiment a Lynx Technologies MDEV-HH LR8 MS 433.92 remote receiver. Any or all of the above described units can be communicatively coupled or connected with any type of wire/cable connection or a Remote 2USB, USB, USB 2.0 or USB3 full duplex connection to the computer 112. The camera tower 104 may also house any or all of the above described units. In one embodiment, the remote control receiver 114 and the remote control unit 107 may not be used to control operations of computer 112.

All of the above described units (e.g., computer 112, camera 102, lights 106, etc.) may be connected to power strip 105 in order to be constantly powered. In one embodiment, a backup power unit may be utilized in tandem with, or in place of, power strip 105 in order to avoid power failure that may compromise recording or that may compromise disk drive performance. Cable housing 113 also houses all cables, wires and connections connecting the various components of human movement analysis system 100 to one another.

Figure 1B:
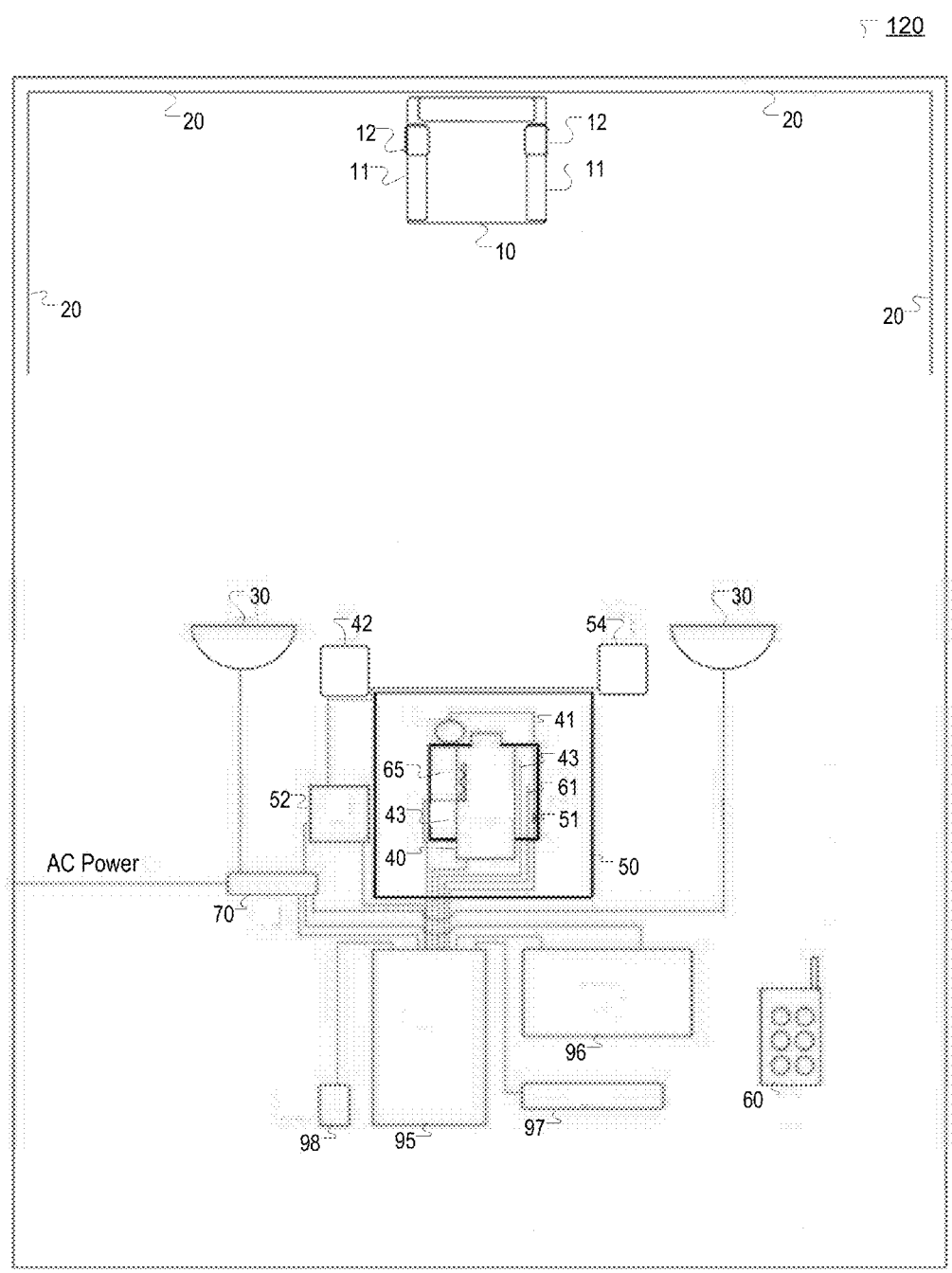
FIG. 1B shows a system for comprehensive human movement analysis according to one embodiment.

FIG. 1B shows a system for comprehensive human movement analysis according to one embodiment. Human Movement Analysis System 120 includes chair 10, cantilevered chair arm 11, elbow holder 12, and elbow holder mounting unit 13 (shown in FIGS. 2D and 2E). Also shown in the human movement analysis system 120 are video wall 20, lights 30, video camera 40, lens hood 41, pan-and-tilt camera mount unit 42, pan-tilt unit controller 43, microphone 50, audio mixer equalizer 51, audio output 52, audio speaker 54, audio instruction sequence 55 (shown in FIG. 3B), remote controller 60, remote controller signal receiver 61, signal light 65, power strip 70, shoe covers 90 (shown in FIGS. 2C, 2D and 2E), host computer system 95, computer monitor 96, keyboard 97, and pointer/mouse 98. In one embodiment, lights 30 may be 2700K lights. In one embodiment, video camera 40 may be 15, 30, 60, 120 or more frames per second and record in color video.

In one embodiment, video camera 40 may use Gigawire, USB or Firewire 111 (IEEE 1394a or 1394b or other 1394-based communications) or engage in wireless communication or be communicatively coupled with the host computer system 95. The frame rate used by video camera 40 for human movement analysis may be from 15, 30, 60 to 120 or higher frames per second, or preferably 30 or above. The image capture software may be capable of processing the digital throughput of the video stream and writing at that speed to the storage media. In one embodiment, video camera 40 may be a color, zoom camera that can be controlled in shutter speed, iris, f-stop, red-white balance, blue-white balance, zoom, gamma, and/or by computer-based control of settings from within the base software. At the beginning of each examination module to be recorded, the host computer system 95 may upload pre-specified camera settings and pan-tilt controller 115 settings for an optimal camera "view", and camera settings for optimal camera positioning, zoom, exposure, shutter and iris settings, and for color-correction. In one embodiment, color information may be stored in the conventional three-plane format of RGB for each pixel in true progressive scan such that each individual frame is a complete image of the scene and subject within the scene. Interlaced format, which may be more common, consists of alternating scan lines of video image information that are from the current frame, alternating with lines of video image information that are from the immediately previous frame. This interlaced format is less desirable for recording human movement sequences, but can be accommodated in the embodiments of the present disclosure with acceptable quantitative data in the results. The color image format for each frame may be provided by the camera 40. In this manner, individual camera settings can be specified for each individual examination module and uploaded to the camera 40 at the initial phase of starting the specific, pre-specified examination test module. In one embodiment, the format for individual frames may be minimally 640×480 pixels, 720×480, 1024×768 or a higher resolution.

Figure 1C:
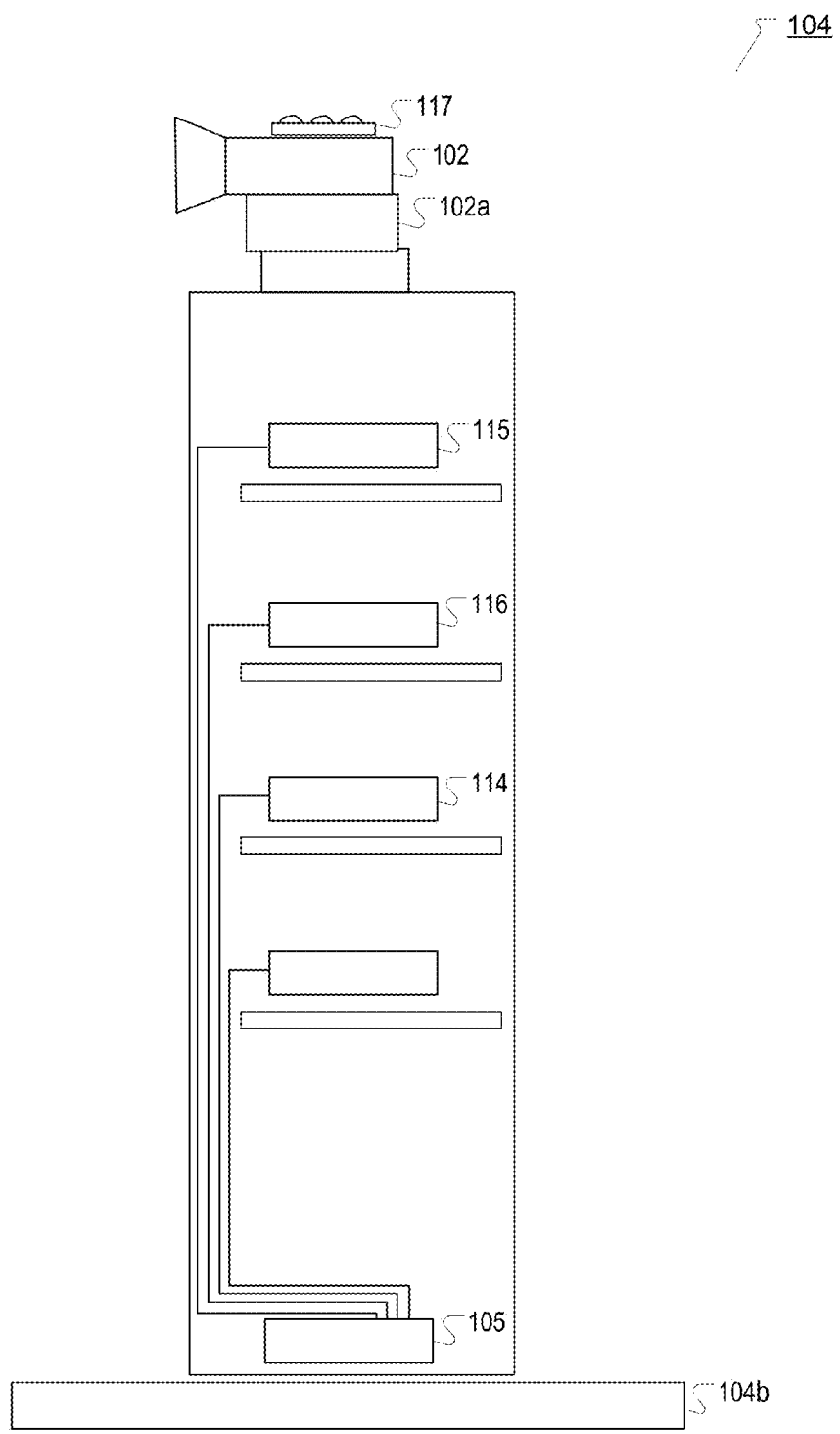
FIG. 1C shows a camera tower used in a system for comprehensive human movement analysis according to one embodiment.
Figure 1D:
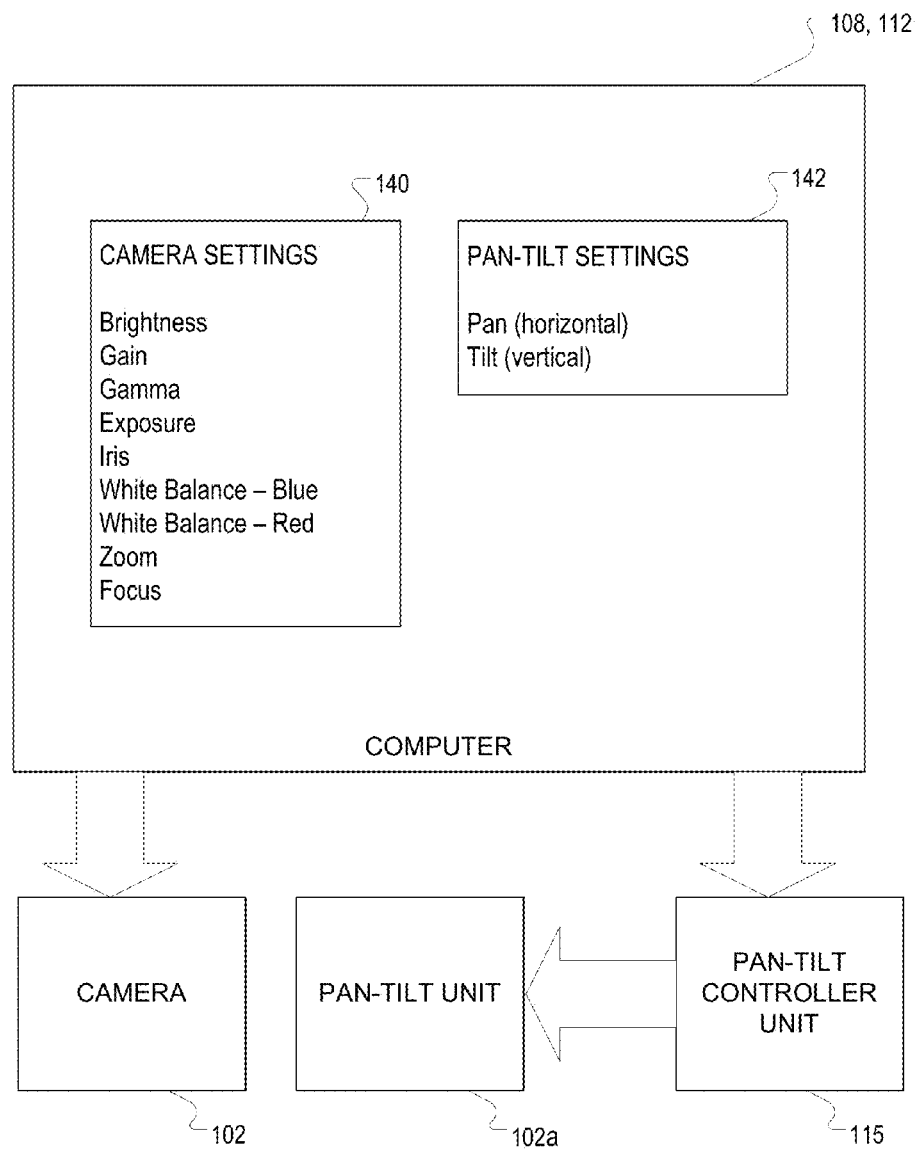
FIG. 1D shows components used in a system for comprehensive human movement analysis according to one embodiment.

FIG. 1C shows a camera tower 104 used in a system for comprehensive human movement analysis according to one embodiment. Camera tower 104 includes signal lights 117, camera 102, pan-tilt unit 102a, pan-tilt controller 115, audio mixer equalizer 116, remote controller receiver 114, power strip 105 and tower base 104b. Signal light 117 provides a signal light to the operator to indicate what operation the computer 112 is currently going through. Camera 102 is the video camera discussed above for recording video and audio, or feeding live video frames to the computer storage 108. In one embodiment, pan-tilt unit 102a may be separate to camera 102 and is used to control the panning (horizontal) or tilting (vertical) movement of the camera 102. In one embodiment, pan-tilt unit 102a may be the same unit as, or attached directly to the camera 102. Pan-tilt controller 115 controls the pan-tilt unit 102a, which in turn controls the panning (horizontal) and tilting (vertical) movement of the camera. Audio mixer equalizer 116 controls the mixing of audio perceived or recorded by the computer 112 and stored in computer storage 108. In one embodiment, microphone 103 may be attached or coupled to the camera 102 to record audio. In one embodiment, the camera 102 may already have audio-recording capabilities to record audio. In one embodiment, microphone 103 may be separate from the camera 102. Remote controller receiver 114 receives signals from the remote control used by operator to control the video camera 102 or objects within the camera tower 104. The power strip 105 provides power to all components in the camera tower 104 and to the camera tower 104 itself. In one embodiment, the camera tower 104 provides physical support and housing for all the above-discussed components and more.

FIG. 1D shows components used in a system for comprehensive human movement analysis according to one embodiment. Computer 112 and computer storage 108 include camera settings 140 and pan-tilt settings 142. In one embodiment, module configuration settings include camera settings 140 and pan-tilt settings 142. Computer 112 and computer storage 108 may also be communicatively coupled to camera 102. Computer 112 and computer storage 108 may also be communicatively coupled to pan-tilt controller 115, which is in turn coupled to pan-tilt unit 102a. In one embodiment, the camera 102 may be separate from the pan-tilt unit 102a. In one embodiment, the camera 102 may be one unit as, or attached to the pan-tilt unit 102a. The pan-tilt unit 102a, controlled by pan-tilt controller 115, controls the pan (horizontal movement) and tilt (vertical movement) of camera 102. Camera settings 140 may include, but are not limited to, settings to adjust: brightness, gain, gamma, exposure, iris, white balance—red, white balance—blue, zoom, focus, frame rate, etc. The pan-tilt settings 142 may include, but are not limited to, settings to adjust pan (horizontal movement) and tilt (vertical movement) of the camera 102.

Figure 2A:
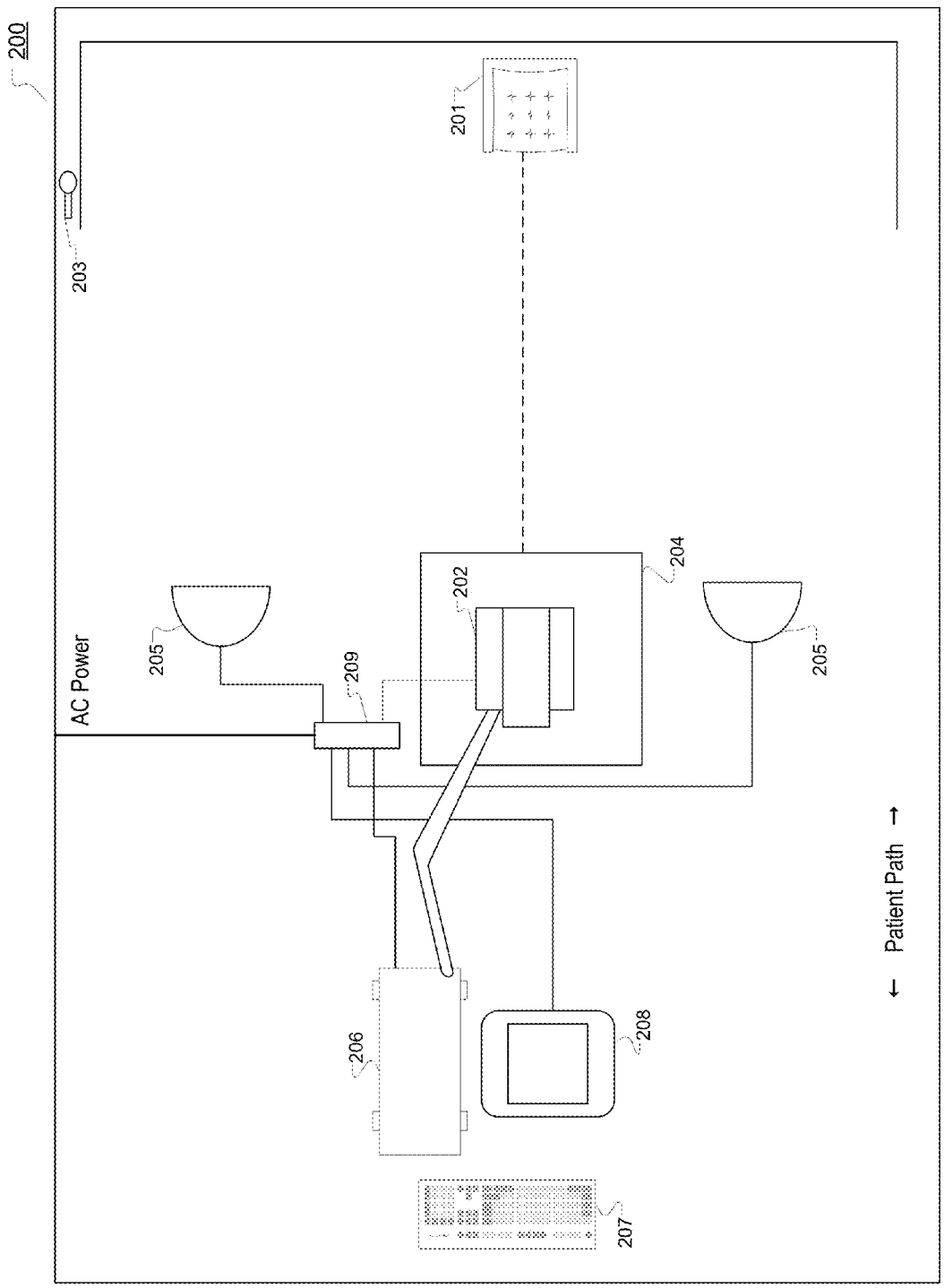
FIG. 2A shows a system for comprehensive human movement analysis according to one embodiment.

FIG. 2A shows a system for comprehensive human movement analysis according to one embodiment. Human Movement Analysis System 200 is a more focused depiction of the system shown in FIG. 1A. In one embodiment, chair 201 is also surrounded or flanked by a video wall including at least one muslin video wall (shown as 10 feet×12 feet merely as an example), and chair 201 is where a patient, object or machine can sit or be placed and be recorded/observed. Microphone 203 is located near chair 201 in order to record any sound data from the patient in the chair 201. As shown in FIG. 2, a distance of 18 feet (shown here merely as an example) can separate the chair 201 from the camera 202. Camera 202 has a tower 204 holding it, and within tower 204, most of the units described in FIGS. 1A and 1C may be housed. Lights 205, similar to the lights described in FIG. 1A, illuminate the subject sitting in the chair 201 in order to increase recording accuracy, and additional ceiling lights (not shown) may be used in tandem with these lights 205. Camera 202 is in turn connected to computer 206, which has a monitor 208 and keyboard 207 connected to it. Any or all of the units described above (e.g., camera 202, computer 206, lights 205, etc.) may be connected to power strip 209 in order to be constantly powered. As shown in FIG. 2A, AC Power may be used to power the power strip 209, but the power is not limited to this particular form of energy.

Figure 2B:
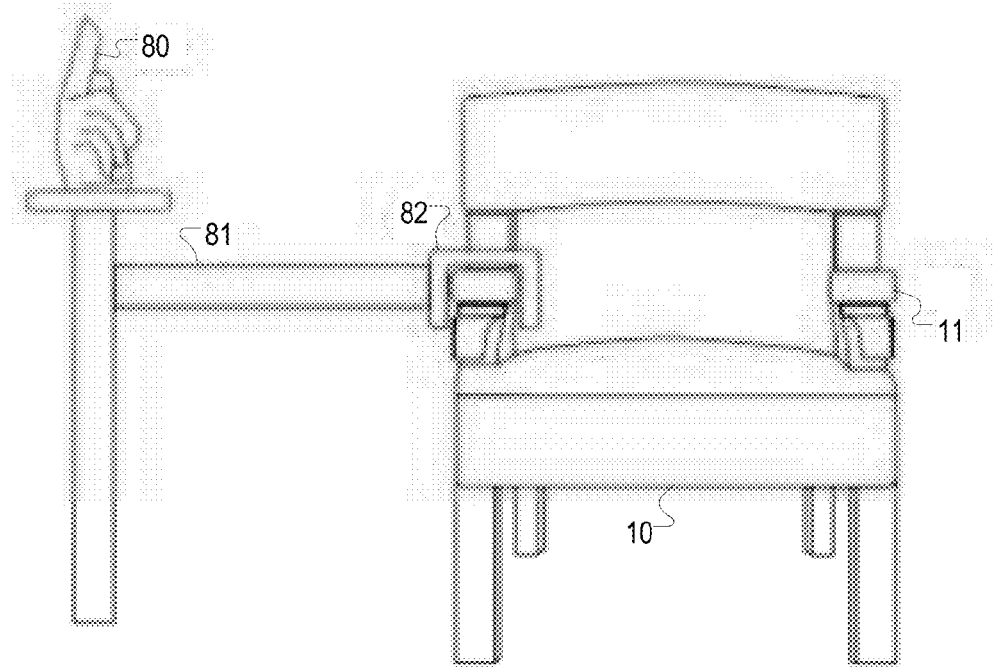
FIG. 2B shows a close-up of a component used in a system for comprehensive human movement analysis according to one embodiment.

FIG. 2B shows a close-up of a component used in a system for comprehensive human movement analysis according to one embodiment. In particular, chair system 220 is shown, which includes chair 10, cantilevered chair arms 11, hand-cast 80, hand-cast mounting unit 81 and hand-cast chair mounting unit 82. In one embodiment, hand-cast 80 may be an artificial object made to realistically resemble a human hand, wherein what is represented is the pliability, size and shape of a real hand in a clenched posture with an index finger pointing up, and further wherein the hand may be made of biologically inert material that accommodates repeated antimicrobial cleaning for patient safety. In other words, the hand-cast 80 may be life-size and made of biologically inert silastic elastomeric material that reproduces the fine detail of a real human hand. The hand-cast 80 may be pliable, supple, may feel just like skin, may be off white in color and semi-transparent, and may have just the right elasticity so as to create a reproducible video-image "artifact" when the patient actually touches the finger of the hand-cast 80 and when the patient's finger touches the patient's own nose on the patient's head, as covered in more detail in the "Finger-to-Nose" module below.

Figure 2C:
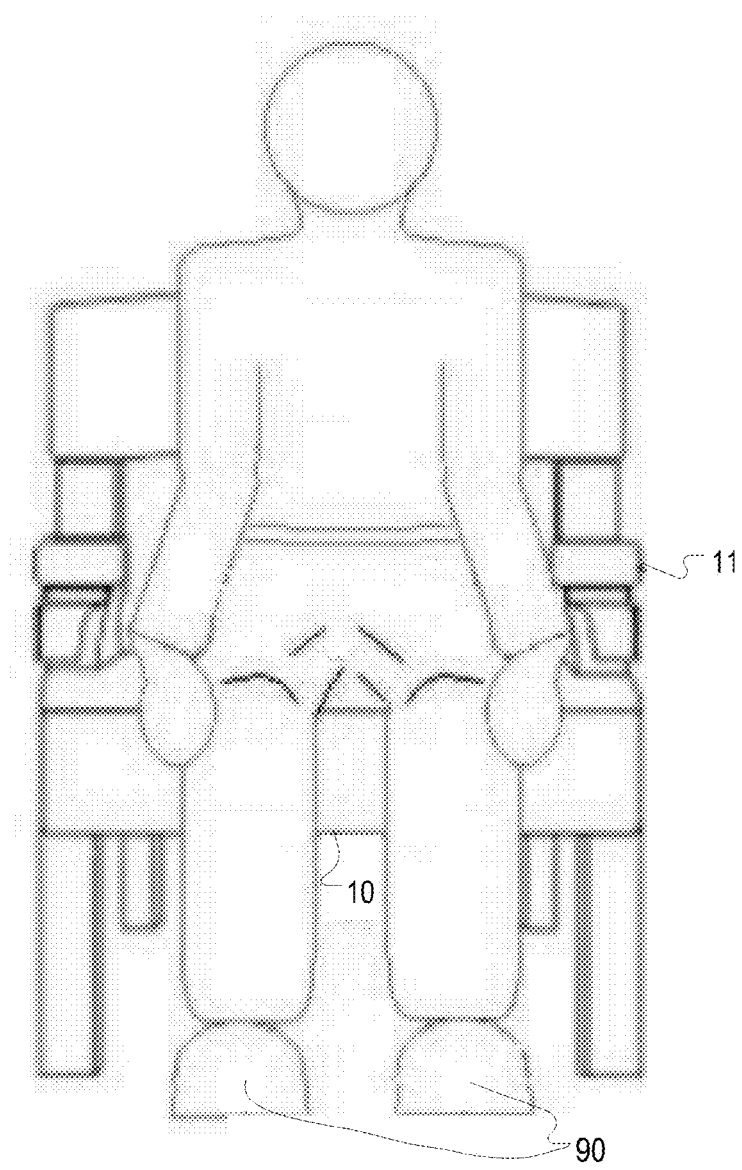
FIG. 2C shows a view of a patient sitting in a component used in a system for comprehensive human movement analysis according to one embodiment.

FIG. 2C shows a view of a patient sitting in a component used in a system for comprehensive human movement analysis according to one embodiment. Patient is sitting in chair 10 and is seen wearing shoe covers 90. The cantilevered chair arms 11 are seen to the left and to the right of the patient.

Figure 2D:
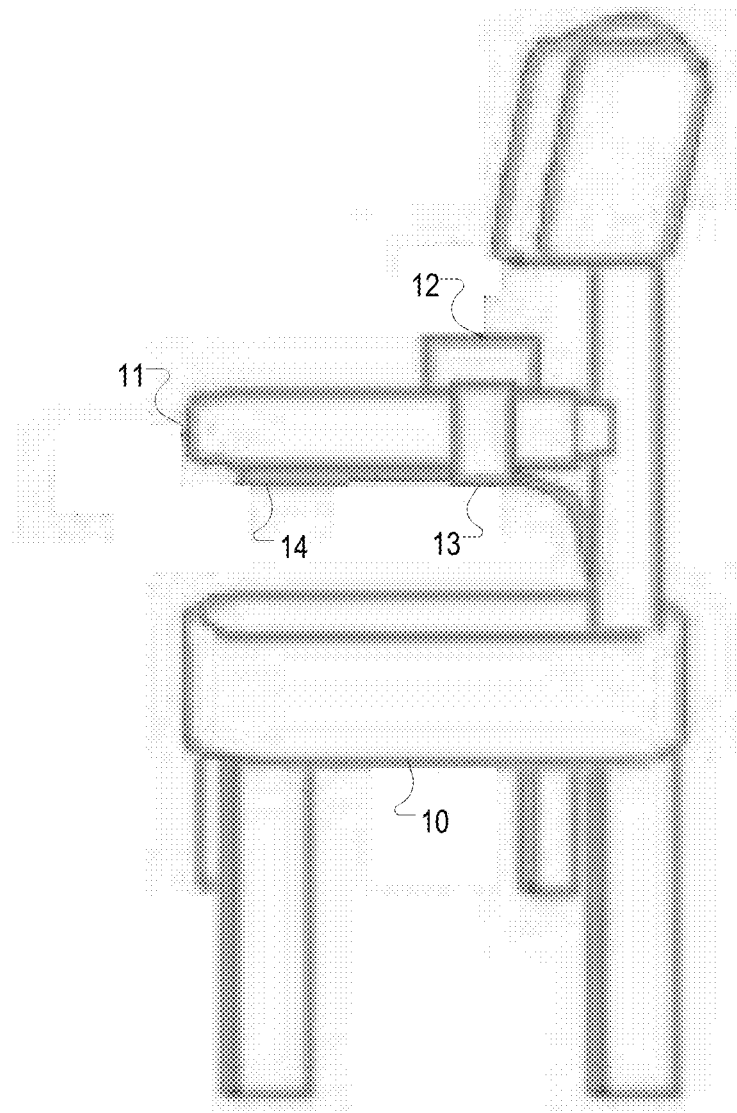
FIG. 2D shows a view of a component used in a system for comprehensive human movement analysis according to one embodiment.

FIG. 2D shows a view of a component used in a system for comprehensive human movement analysis according to one embodiment. FIG. 2D illustrates a side-view of the chair 10. Now visible, in addition to the cantilevered chair arm 11, are elbow holders 12, elbow holder mounting units 13, and support arch 14. Elbow holders 12 and elbow holder mounting units 13 allow the patient to comfortably support his or her elbow within a safe resting place. Support arch 14 allows safe support of the cantilevered chair arms 11 while allowing the patient to sit frontwards-facing in the chair 10, or to sit sideways-facing in the same chair 10 with his or her legs extending perpendicular to the camera-chair axis with the legs passing underneath the arm of the chair 10.

Figure 2E:
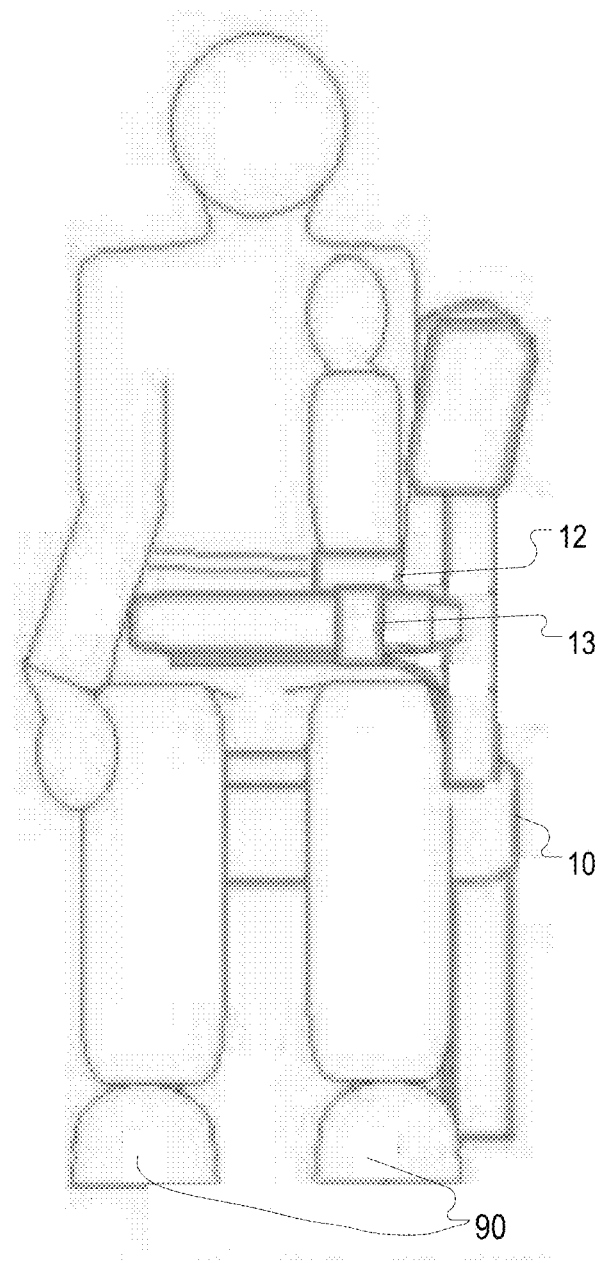
FIG. 2E shows a view of a patient sitting in a component used in a system for comprehensive human movement analysis according to one embodiment.

FIG. 2E shows a view of a patient sitting in a component used in a system for comprehensive human movement analysis according to one embodiment. Now the patient, wearing shoe covers 90, is shown sitting in the chair 10 with his or her arm resting on the elbow holder 12 and the elbow holder mounting unit 13. Although the support arch 14 is not shown in FIG. 2E, they help support the elbow holder 12 and elbow holder mounting unit 13 and also allow the patient to sit in any direction that is convenient.

Recording System Overview

Figure 3A:
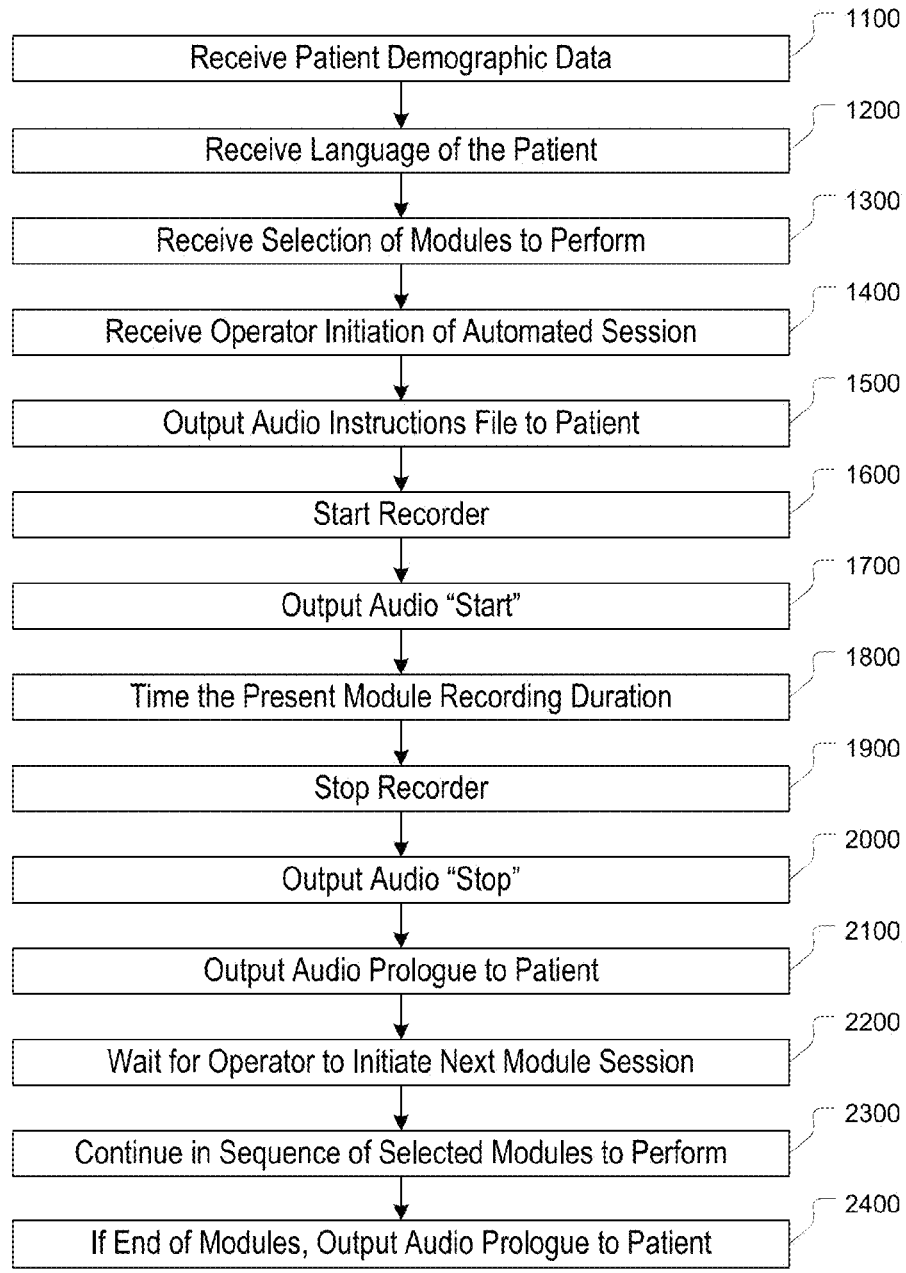
FIG. 3A shows a flowchart of a method for a recording system overview used for comprehensive human movement analysis according to one embodiment.

FIG. 3A shows a flowchart of a method for a recording system overview used for comprehensive human movement analysis according to one embodiment. Recording system overview method 1000 is the recording system method that records movement data from a subject/patient (or object, animal or machine) and includes the below described steps.

In step 1100, demographic data about the subject or patient is received, the patient demographic data including name, gender, age, ethnicity, nationality, previous medical history, medication taken, chart number, patient identification number, diseases and previous medical data. Ethnicity and nationality are helpful in gauging different "styles of movement" that vary across cultures for the analysis of different movement abnormalities or diseases.

In step 1200, a selection of language of the patient is received for identification/categorization and diagnosis purposes, and also to aid the audio instruction interface that a subject may interact with when being video-recorded (for example, audio instructions that are presented to the subject in the language(s) best understood by the patient to tell them "what to do", "how often", "when to do it", "when to start" and "when to end", and when the procedure has ended). If the language preferred by the patient is not available in its entirety, or in one or more modules, each such module may default to English audio instructions, then resume in the desired language with the next module that is available in that desired language.

In step 1300, the selection of modules to perform is received. Once the desired human movement analysis module is selected, the camera may be set up, along with any props in the subject area 101, according to the selected human movement examination module and human movement examination item to be executed and analyzed. The recording system records the data as it is set-up, and the analysis system takes this recorded data and analyzes the data assuming that certain settings have been established in the recording.

In step 1400, the operator initiation of the automated session is received. The operator initiation includes the positioning of the patient or the object to be examined. For example, the patient may be directed to sit in a chair, as shown in the previous Figures, or may be asked to stand up and walk. The patient may also be asked to move their hands or feet, or sit still to observe tremors that occur naturally. The system in step 1500 recites an audio instruction file to the patient in the language that is determined from step 1200, telling the patient that the session is about to begin and instructing the patient on what he or she is to do, and also when to start, and when to end the performance of the instructed movement.

Then, in step 1600, the recorder is started (e.g., the camera starts recording and audio recording also starts with a separate microphone or audio-recording component on the camera). In one embodiment, the camera 102 does not record but rather feeds live video into the computer 112 and the computer 112 uses a frame capture application to write video frames and incoming sound to a computer storage device, for example computer storage 108. In one embodiment, the microphone 103 may be live at all times and only in step 1600 does the computer begin to write incoming sound to a computer storage file. In step 1700, the audio instruction file outputs an audio "Start", audibly signaling the time for the patient to begin performing the movement described in step 1600. In one embodiment, the audio instruction "Start" is output to audio speakers (amplifiers 52 and speakers 42 and 54) for reception by the patient. In step 1800, the system timing of a preset module recording duration executes and then expires, which establishes that all the data has been recorded for this module. Then, in step 1900, the recorder is stopped, and in 2000, the system outputs an audible "Stop". In step 2100, an audio prologue (delivered in the language determined from step 1200) may be recited to the patient, describing to the patient that the recording is over and has been completed, and any additional post-session instructions. In step 2200, the system can wait for the operator to initiate the next module. In the next module, the operator can, in step 2300, continue to the next selected module in a sequence of selected modules to perform. In step 4500, once the end of the selected modules has been reached and all the selected modules have been performed, an audio post-session presentation prologue (delivered in the language determined from step 1200) is recited to the patient as the last segment of the audio instruction file started in step 1500.

Figure 3B:
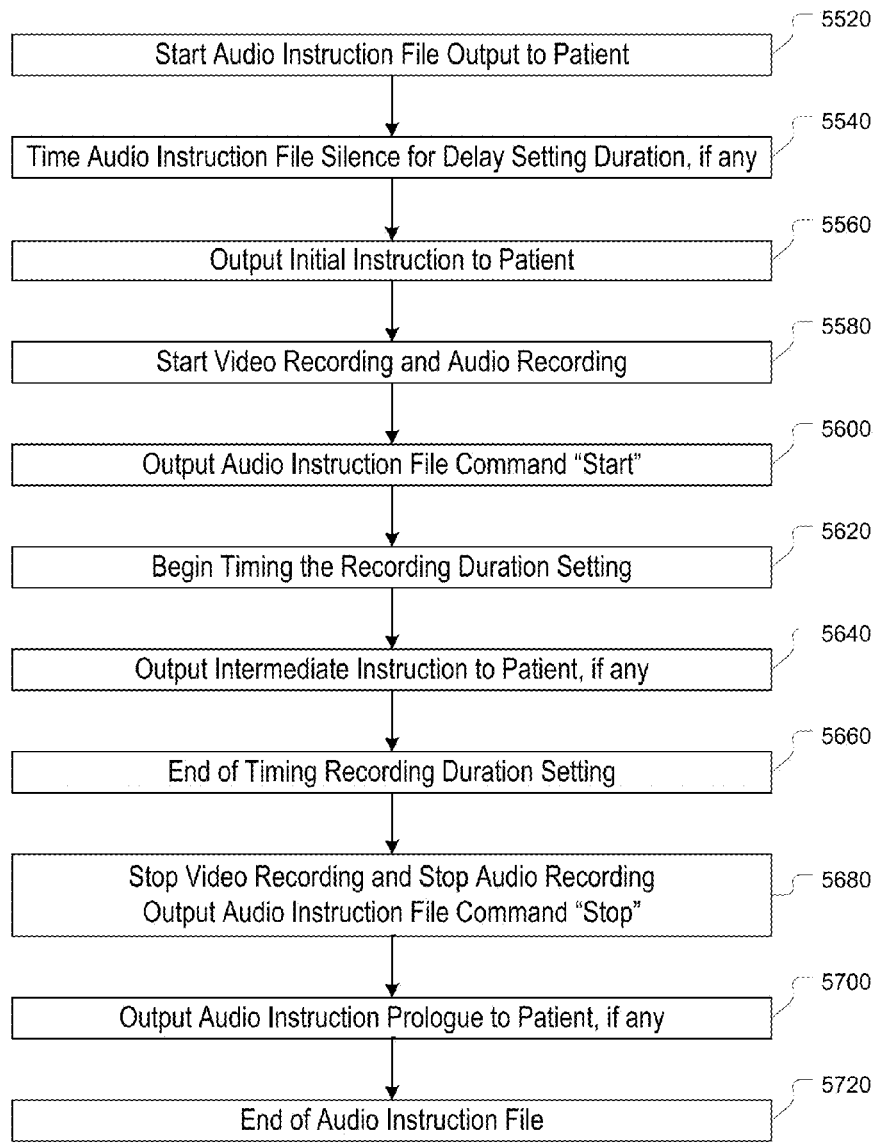
FIG. 3B shows a flowchart of a method for an audio instruction overview used for comprehensive human movement analysis according to one embodiment.

FIG. 3B shows a flowchart of a method for an audio instruction overview used for comprehensive human movement analysis according to one embodiment. Audio instruction sequence 55 begins in step 5520, where the system starts audio instruction file play output to the patient. In step 5540, there is a time duration audio-instruction file silence for a delay, if any delay should be specified for the module. In step 5560, initial audio instructions are outputted or recited to the patient. In step 5580, video recording is started and audio recording is also started by the computer 112. In step 5600, the audio instruction file command outputs or recites a "Start" command via, for example, the audio speakers 42, 54. In step 5620, the timing of the recording duration setting begins and the computer-timed recording period begins. In step 5640, the intermediate instruction command is outputted, if any. In step 5660, the computer-timed recording duration ends. In step 5680, the video and audio recording stops, and the audio instruction file command outputs a "Stop" command to the patient. In step 5700, the prologue audio instructions are output to the patient, if any. In step 5720, the end of the audio instruction file is reached.

In one embodiment, an audio instruction file storing an audio instruction sequence 55 is a pre-recorded audio instruction file for play out to an audio output device 52, as shown in FIG. 1B. The audio instruction file having audio instruction sequence 55 is specific to a particular human movement examination module and to the examination item served by that module. The audio instruction sequence 55 contains several sections, and has timing points that coordinate and are synchronous in timing with the video and audio recording delay and onset, with the video and audio recording duration. The minimal structure is the audio-video recording delay period, the audio vocal phrase "Start" at the beginning of the audio-video recording phase of the module, a quiet period of duration equal to the audio-video recording duration, the word "Stop" at the end of the audio-video recording phase duration, then the end of the audio instruction file. Additional audio information may consist of words of encouragement (e.g., "good"), words of comfort (e.g., "just relax"), intermediate instructions during the performance of the instructed item (e.g., "when you reach the wall, stand facing the wall") or prologue phrases (e.g., "now, please continue to stand") following the word "Stop".

The following description of an audio instruction file to store an audio instruction sequence 55 is illustrative by way of example and not to be construed as a limitation. In one embodiment, audio instruction sequence 55 may be stored in computer storage 108 of the computer 112 or in another storage form which computer 112 has connectivity and access to. The present disclosure includes pre-recorded audio instructions to the patient in any language. Prior patents or published literature may have disclosed the use of pre-recorded audio instructions to a patient. What is unique in the present disclosure is that audio instructions are structured to include timing information, built-in latencies to begin performance, and timing signals to the patient and to the operator conducting the study with the patient. In one embodiment, the pre-recorded audio instruction may contain specific timing marker tones and specific timing data to constrain the time of movement actions in each examination module. For example, the audio file begins to play output to the patient or object of the recording via the audio output device 52 and audio speaker 54. The beginning may be a long silence, or a detailed description of the movement to perform, followed by the word "Start" in the preferred language that coincides with the beginning of the video and audio recording executed by the system. After a pre-set timing delay, the movement performance period, at the time delay coinciding with the completion of the video and audio recording actions, the word "Stop" in the preferred language is recited and the audio file ends or may play a "prologue" telling the patient what to do next to prepare for the successive module, if any.

The first specific timing data is the duration of the main instruction onset and duration. To accommodate a number of languages, the initial instruction in the examination module may present the initial instruction to the patient, followed by a preparatory command, followed by the "Start" command, then a duration that is the time duration allowed for the performance of the examination item as instructed, followed by "Stop", then the instruction to "relax" or "put your arms down" (e.g., to cease the posture instructed for the examination item just performed), followed by the preparatory instructions for the subsequent module. There are some modules that use an intermediate instruction at some point in time during the performance of the movements in the module, such that the individual is aware of what is expected of the individual at the end of the performance.

The timing of these audio instruction file elements and the signals used to begin and to end the movement performance instructed are placed in specific timing points in the sequence of the audio instruction file 55 to ensure that the performance begins and ends in the expected manner and that is also synchronous with the recording of the audio and video (started in step 5580), which begins and ends at specific timings that are pre-set in the timing parameters of the computer software controlling various module configuration settings, including the pan-tilt settings 142, and camera settings 140 including the camera iris, exposure settings and white balance, and the initiating 5580 and ending 5680 of the audio and video recording during the movement examination item performance.

In one embodiment, in some movement examination items, for example, it may be desirable to start recording the audio and video when the performance of the movement items is in progress. In that case, the audio and video recording 5580 is started at a short delay from the moment of the audio instruction command "Start" 5600, following the initial audio instructions 5520. In other examination items it may be desirable to determine the latency to start performing the instructed item so that the audio and video recording 5580 is set to begin a fixed time interval before the word command "Start" occurs (5600) in the audio instruction sequence 55 stream. In one embodiment, the audio instruction allows a fixed pre-performance time interval to be in the resulting video record such that the latency for the individual subject to start the movement performance is the fixed item interval from the start of the audio and video recording 5580 to the command to "Start", plus the patient's delay in the start of the movement performance beginning with the audio instruction word to "Start". In this manner, the analysis of the record can determine the net "latency" to begin the movement performance by subtracting the fixed time interval from the time to the first movement of the instructed type. Audio instruction sequences 55 in different languages must conform to a standard for timings that is specific to the individual model, but that is independent of the language of the instruction to the individual performing the examination item. To accommodate this standard, it is beneficial to determine the overall length of the audio instruction segments for a specific module, and to set the duration of those segments within the audio instruction sequence 55 for the examination module to the longest instruction time from among the languages represented. In this manner, some languages will have a shorter initial audio instruction than others for the same examination module, and the languages that have shorter than the longest time length for that segment in that specific examination module will start later in the audio instruction sequence 55 than the longest duration language instruction for that segment of the audio instruction sequence 55.

For languages that have shorter than the longest duration for that segment, the end of each initial language audio instruction segment will be placed at the same total audio instruction sequence 55 segment elapsed-time point, such that the end of that initial audio instruction segment will always occur at the same time duration from the beginning of the audio instruction track for that specific examination module. In some languages then, the duration of the specific audio instruction segment will be less than the maximum among the languages represented, and the result will be the presence of no audible sound from the beginning of the audio instruction sequence 55 to the beginning of the audio instruction in that language. The end of the initial audio instruction segment will be at the same duration from the beginning of the audio instruction track, such that the point of the preparation command (such as "Ready") and the subsequent command "Start", can occur at the same time in every language, and the duration between "Start" and "Stop" will always be the same as the audio-video recording duration setting. Blank spaces can be filled with very small, amplitude-bearing, audible, 0.2 second duration "beep" sounds at one-second intervals until the verbal audio instructions begin for a specific language. This fulfills the purpose of letting the operator and the individual performing the instructed movement examination item be informed that the examination module is active and continuing.

Analysis System Overview

Figure 4A:
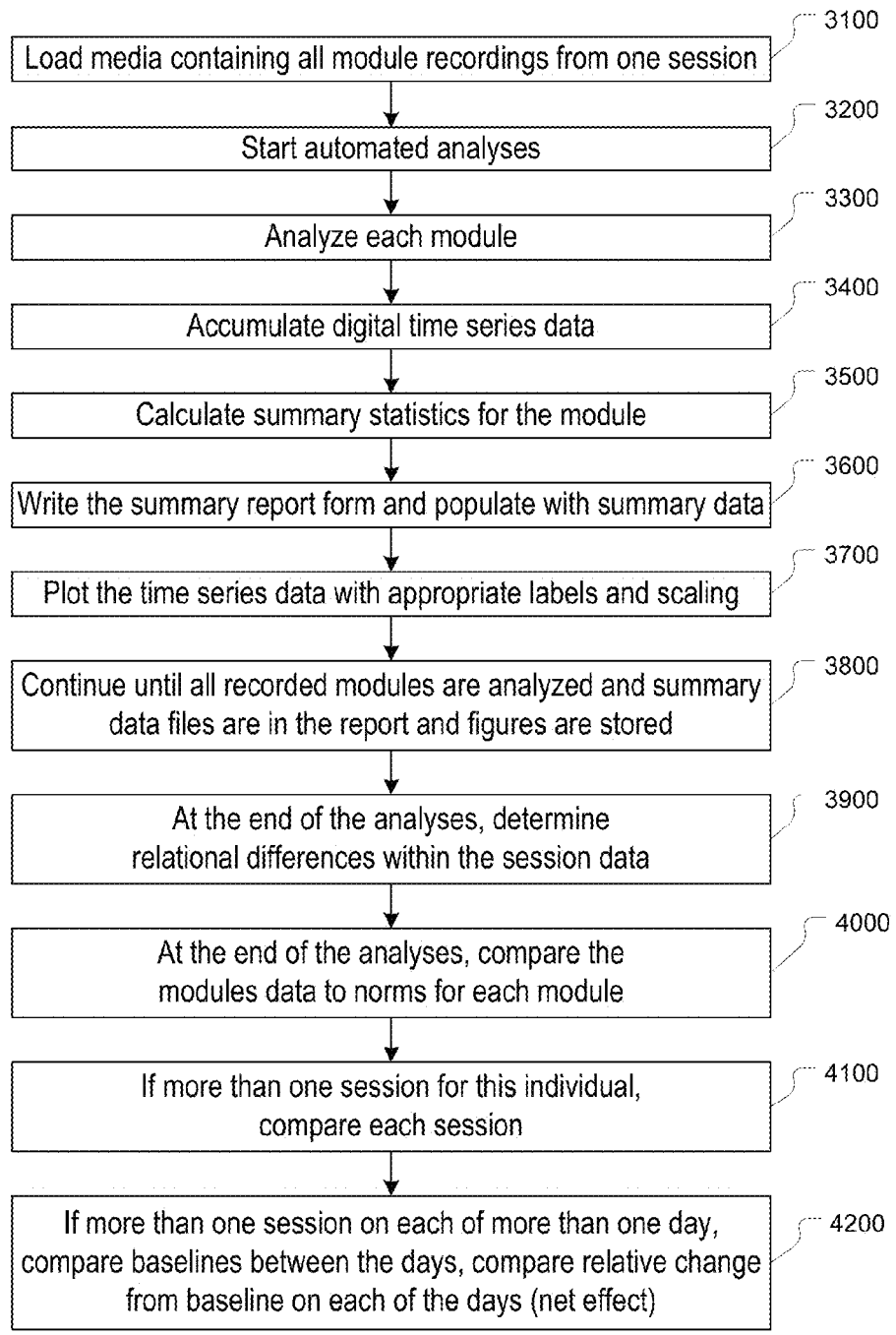
FIG. 4A shows a flowchart of a method for an analysis system overview used for comprehensive human movement analysis according to one embodiment.

FIG. 4A shows a flowchart of a method for an analysis system overview used for comprehensive human movement analysis according to one embodiment. Analysis system overview method 3000 is the analysis system used by the human movement analysis module that analyzes the recorded data that has been recorded from a subject or patient (or object, animal or machine) during the recording system detailed in FIG. 3A. The analysis system overview method 3000 includes the steps described below.

In step 3100, the recorded media containing all the module recordings from a single session (such as the session run in FIG. 3A) is loaded into a computer system. In step 3200, automated analyses are initiated to access the loaded data on the storage media. The analysis system method is divided into human movement analysis modules (as is the recording; the analysis is tailored according to the module that is to be analyzed). In step 3300, each module is analyzed in turn, the analysis of each module employing a series of sophisticated, advanced algorithms and heuristics that will be detailed below. The bulk of the flowcharts and descriptions in this application will focus on the individual modules employed in the recording system and analyzed in the analysis system method.

In step 3400, after all the modules have been analyzed, the digital time series data from each module will be accumulated. In step 3500, the summary statistics are calculated for each module. For example, in step 3600, the summary report form is written and populated with summary data. A summary report form is a compilation of numerical data output by each analysis. In step 3700, the time series data is plotted with appropriate labels and scaling. In step 3800, the generation of the summary report forms and the plots is continued until all the recorded modules (from FIG. 3A) are analyzed and all the summary data files are in the report and all the figures are stored. In step 3900, at the end of the analysis, the relational differences within the compiled session data (from step 3800) are determined. In step 4000, at the end of the analyses, the data from the modules are compared to the norms for each module. In step 4100, if there is more than one session for this individual, then a comparison is made between the different sessions run for this individual. Finally, in step 4200, if there is more than one session on each of more than one day, then the process may compare the baselines between the days, or if more than one session for each of those days, compare the relative changes from the baselines on each of these days to determine an overall net effect for each day and net effects across days.

Figure 4B:
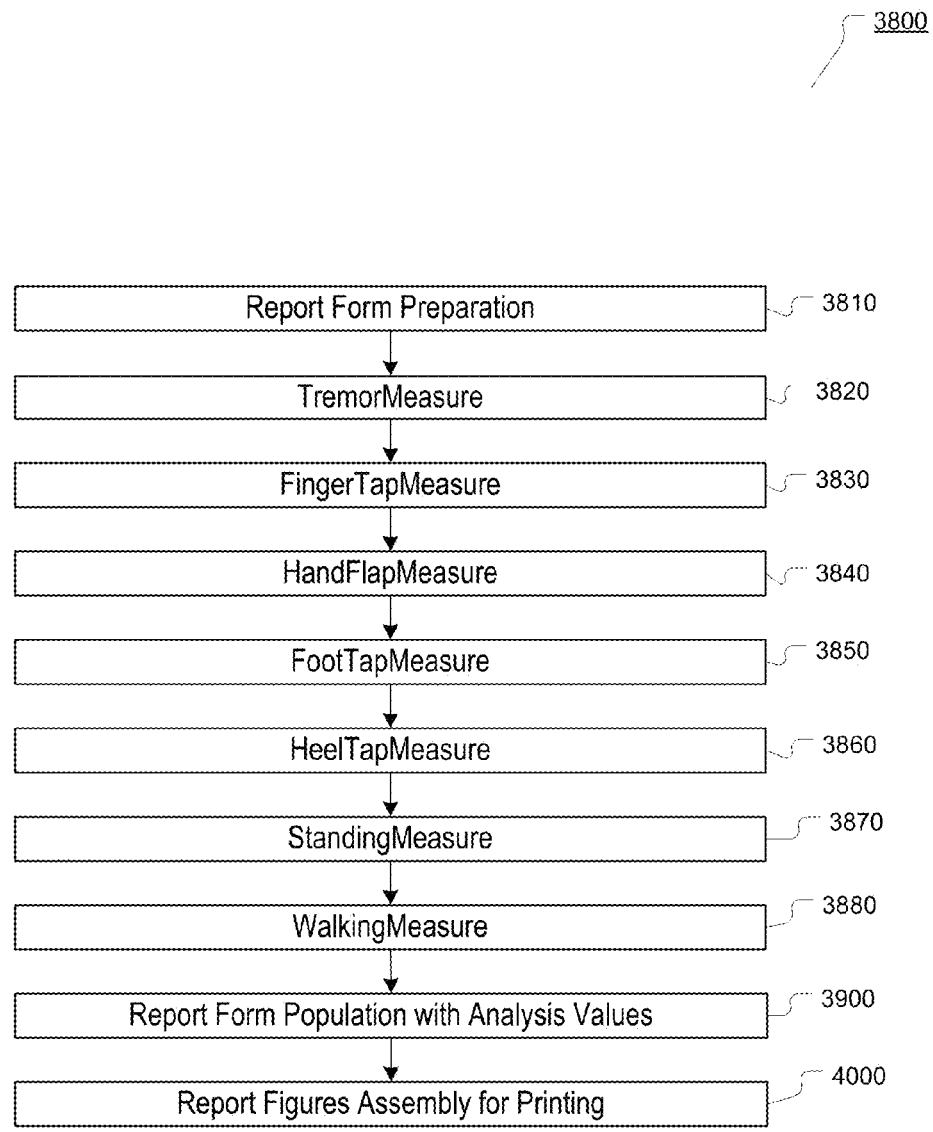
FIG. 4B shows a flowchart of a method for analysis modules and generating report forms and report figures, used for comprehensive human movement analysis according to one embodiment.

FIG. 4B shows a flowchart of a method for analysis modules and generating report forms and report figures, used for comprehensive human movement analysis according to one embodiment. As described above, the analysis modules 3800 are human movement analysis modules for which the recording system (FIG. 3A) is set up to run and record data, and which are in turn analyzed with different human movement analysis modules—each module comprising a different set of algorithms and heuristics. For example, an exemplary list of human movement analysis modules is provided in 3810-3880. In one embodiment, additional modules may be performed in 3810-3880, which may be, but are not limited to: Extended Arm Hand Tremor Excursions, Hands Alternating Pronation-Supination, Finger-to-Nose Excursions, and Body Stability with Shoulder Displacement. Furthermore, it is important to note that the analysis modules are certainly not limited to the ones described above or below in this present disclosure. Report Form Preparation 3810 is a basic analysis module that simply sets up the form and data to be ultimately output in a report form. The other analysis modules of TremorMeasure 3820, FingerTapMeasure 3830, HandFlapMeasure 3840, FootTapMeasure 3850, HeelTapMeasure 3860, StandingMeasure 3870 and WalkingMeasure 3880 will be described below in more detail. After any or all of these analysis modules are run on recorded data, in step 3900 report forms are populated with the acquired analysis values, and the report figure plots are then assembled for printing in step 4000. In one embodiment, these steps are essentially the same as the last several steps in FIG. 4 (the generation of the summary reports and the plots) but they are simply repeated here again in order to clarify that these steps are performed after any or all of the analysis modules have been completed.

Now, an exemplary number of the main modules will be described in further detail. Any of the below described modules may be utilized as the analysis modules that have been described above.

Foot Agility Analysis: Foot Tapping and Heel Tapping

Figure 5:
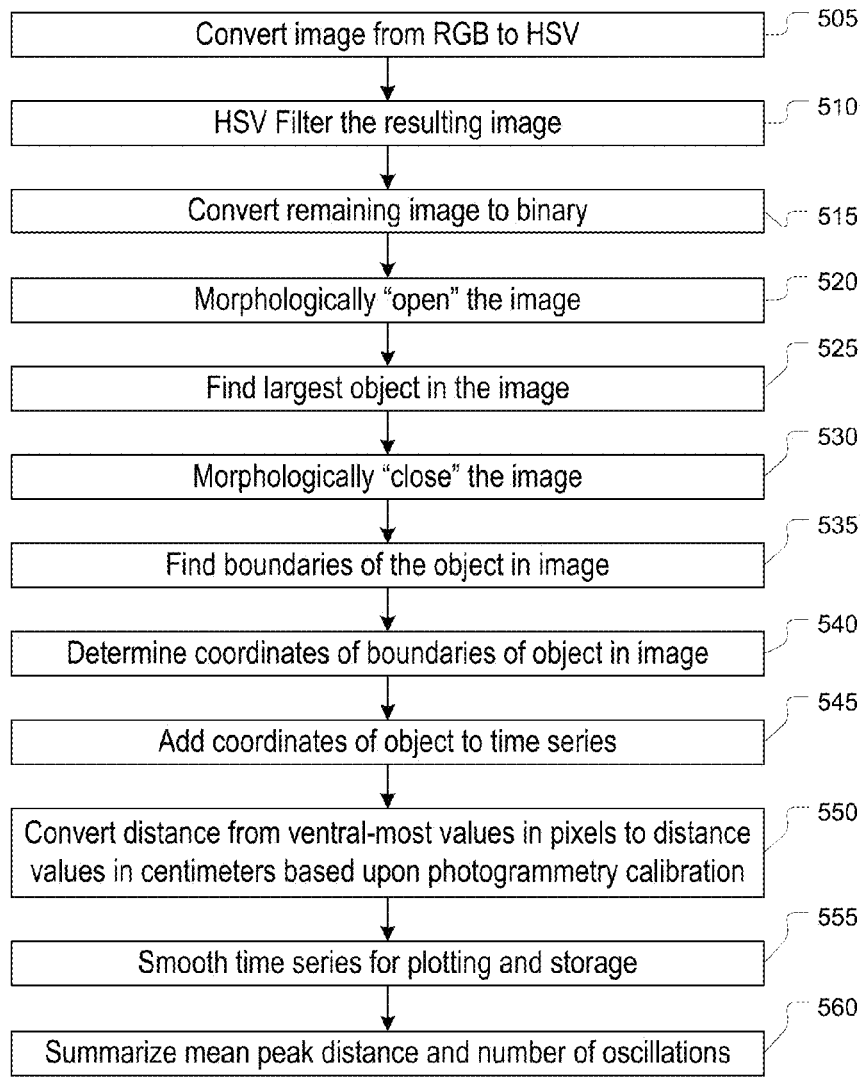
FIG. 5 shows a flowchart for a foot and heel tapping analysis method for comprehensive human movement analysis according to one embodiment.

FIG. 5 shows a flowchart for a foot and heel tapping analysis method for comprehensive human movement analysis according to one embodiment. Foot Tapping and Heel Tapping process 500 can be performed separately for the left foot and the right foot. The process 500 may be applied to up to four different modules out of the analysis modules described previously. The process 500 performs its steps on individual frame images taken from a recorded video file sequence. Therefore, in one embodiment, within each frame image, the following steps are performed: in step 505, the frame image is converted from RGB (Red Green Blue) to HSV (Hue Saturation and Value). HSV is a color representation of points transformed from an RGB color model. In step 510, an HSV filter must be performed on the resulting image. In step 515, the remaining image resulting from the HSV filter in step 510 is converted to binary form. In step 520, the image is morphologically opened or dilated. In step 525, the largest object in the image is found. In step 530, the image is morphologically closed. In step 535, the boundaries of the largest object are found in the image. In step 540, the coordinates of the boundaries of the largest object in the image is determined. In one embodiment, the boundaries of the largest object in the image may be the ventral-most or most front or anterior boundaries of an object. In step 545, the coordinates of the object determined in step 540 are added to a time series. In step 550, the distance from the ventral-most values to the floor in pixels is converted to distance values in centimeters based upon calibration, for example, photogrammetry calibration. In step 555, the time series (which accumulates the coordinates of objects mentioned in step 545) is smoothed for plotting and storage purposes. In step 560, the mean peak distance (height) and number of oscillations is summarized. In one embodiment, HSV, for example, may not be used in the above steps but other color filtering processes used.

Usually, in order to analyze foot tapping and heel tapping, the patient is given shoe covers 90 (that absorb or reflect specific light wavelengths during recording efforts) to wear on their shoes or feet. Shoe covers 90 can be substituted with shoe-mounted lasers or LED lights as markers to be tracked by the above-described process 500. The colors of the shoe covers 90 or the LED lights can be red, yellow, green or blue or any pair-wise combination among these in order to maximize visibility for camera recording purposes. Each foot may have a different color shoe cover 90 or LED light to aid tracking and measurement of movement. In one embodiment, color is placed over the shoes to provide a tracking target of two separated colors, one for each foot—this can be performed by attaching different colored covers, markers or LED lights to the feet or shoes of the patient. In other words, colored objects are used to discriminate between the left and right foot for all foot movement items examined. In one embodiment, the coordinates of a "red" object, for example, may be limited at the ventral (front or anterior) extreme of the movement by the floor. The patient is sitting, so the tapping foot, even when stationary, may be floor-limited. Vertical movement of the feet may be limited only by the skeletal length of the leg-foot and the muscle activity of the patient to move the foot up and then down to the floor. In one embodiment, the shadow on the bottom of the foot may be more important than the bulk object of the foot. In one embodiment, the coordinates of greatest interest may not be limited to the ventral extreme of the movement by the floor and instead may focus on different regions or boundaries of the foot. The distinguishing characteristics of the present disclosure's video tracking of colored spots and objects over the prior art include providing distinctive characteristics to each of the feet and to allow automatic tracking of the individual feet in walking, tapping, stepping in a gait and related foot movements.

As an optional decision in process 500, and in order to determine movement "overflow" or over-measurements in an opposite foot, additional steps may be added to step 510, described above. For example, in one embodiment, in step 510, the HSV filter can be performed over the image twice, once for each colored shoe cover 90, and all subsequent operations may then be performed in duplicate for parallel determinations of the shoe cover of the opposite (left and right) foot. The above process 500 may also be used to determine the distance between both feet while a patient is standing in a stationary position.

Hand Agility Analysis: Finger Tapping, Hand Flapping

Figure 6:
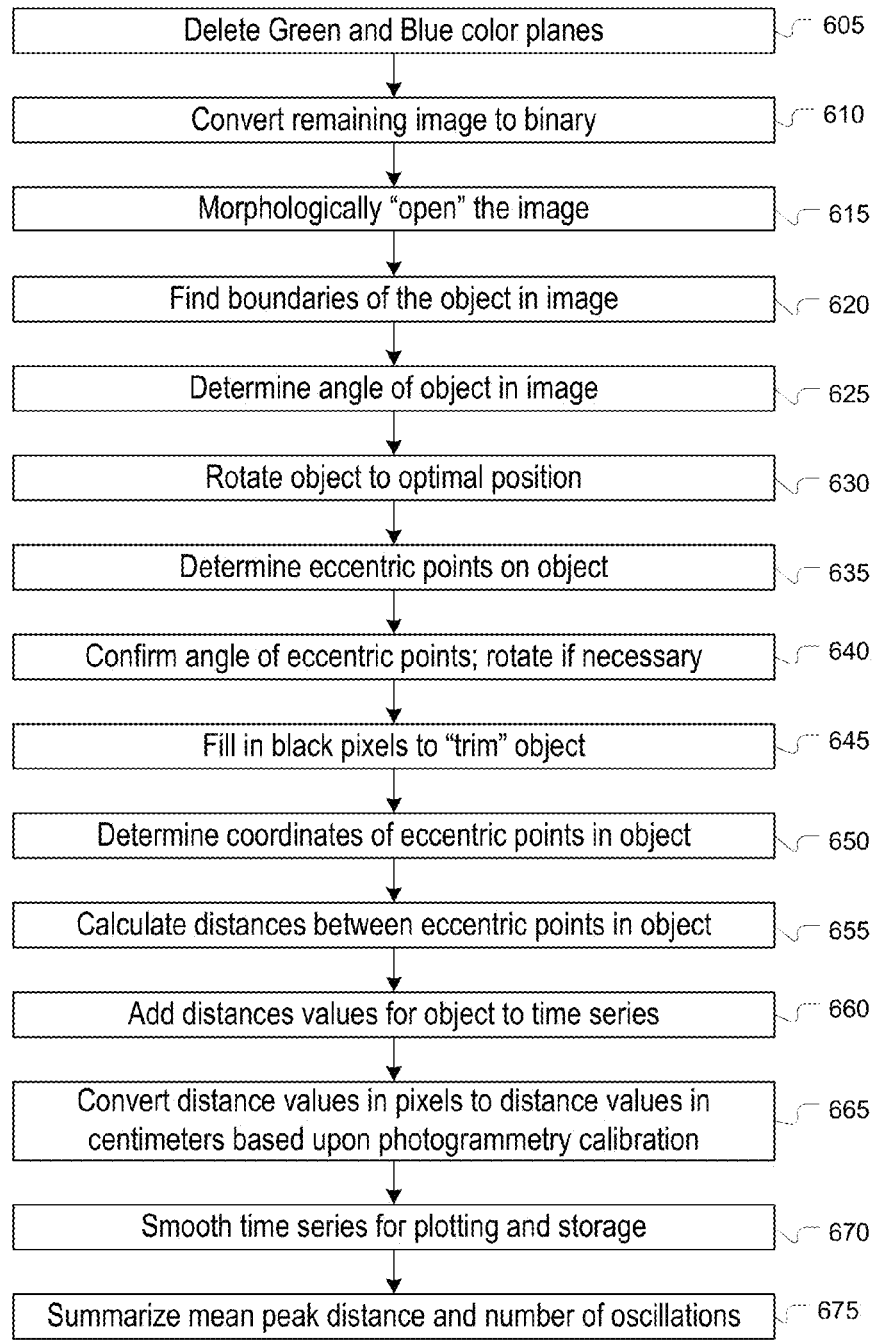
FIG. 6 shows a flowchart for a finger tapping and hand flapping analysis method for comprehensive human movement analysis according to one embodiment.

FIG. 6 shows a flowchart for a finger tapping and hand flapping analysis method for comprehensive human movement analysis according to one embodiment. Finger Tapping and Hand Flapping process 600 can be performed separately for the left hand and the right hand. It is to be noted that Finger Tapping and Hand Flapping are separate processes, but they will be referred to as process 600 for simplicity. In one embodiment, the process 600 may be applied to up to four different modules out of the analysis modules described previously. The process 600 performs its steps on individual frame images taken from a video file sequence. Therefore, within each frame image, the following steps are performed: in step 605, the green and blue color planes of the image frame are deleted. In step 610, once the image has its green and blue color planes removed, the resulting image is converted to binary form. In step 615, the image is morphologically opened or dilated. In step 620, the boundaries of the largest object in the image are found. In step 625, the orientation angle of the largest object in the image is determined. In step 630, the object is rotated to an optimal position. In step 635, the eccentric points of the object are determined. In step 640, the angle of the eccentric points are confirmed, and the object can be rotated to more accurately achieve the desired angle. In step 645, the black pixels of the object are filled in at extraneous regions of the object, in order to "trim" the object. In step 650, the coordinates of eccentric points of the trimmed (black pixel partially filled-in) object are determined. In step 655, the distances between the eccentric points of the trimmed object are calculated. In step 660, the distance values for the object are added to a time series. In step 665, the distance values in pixels (obtained from step 660) are converted to distance values in centimeters based upon calibration, for example, photogrammetry calibration. In step 670, the time series (where distance values for the trimmed object are added to in step 660) is smoothed for plotting and storage purposes. Finally, in step 675, the mean peak distance of the distance between the thumb and index finger, or the distance between the fingertips and the palm of the hand, and number of oscillations is summarized. In one embodiment, the process 600 may be applied to just the thresholded object and the eccentric-points coordinates of the object in each frame, instead of an approach based on the open and morphological hand-line. This approach may use the x and y coordinates in order to be sensitive to tremor movements, as well as finger and hand flexion-extension movements.

In one embodiment, the strategy of the above-described process 600 utilizes the red color plane of the RGB images. In essence, skin color is not determined, and the strategy of process 600 permits the detection of a hand against a background where the hand belongs to an individual with many different types of skin "color" and "tone", ranging from heavily pigmented to almost no pigmentation.

Head Movement Measuring

Figure 7:
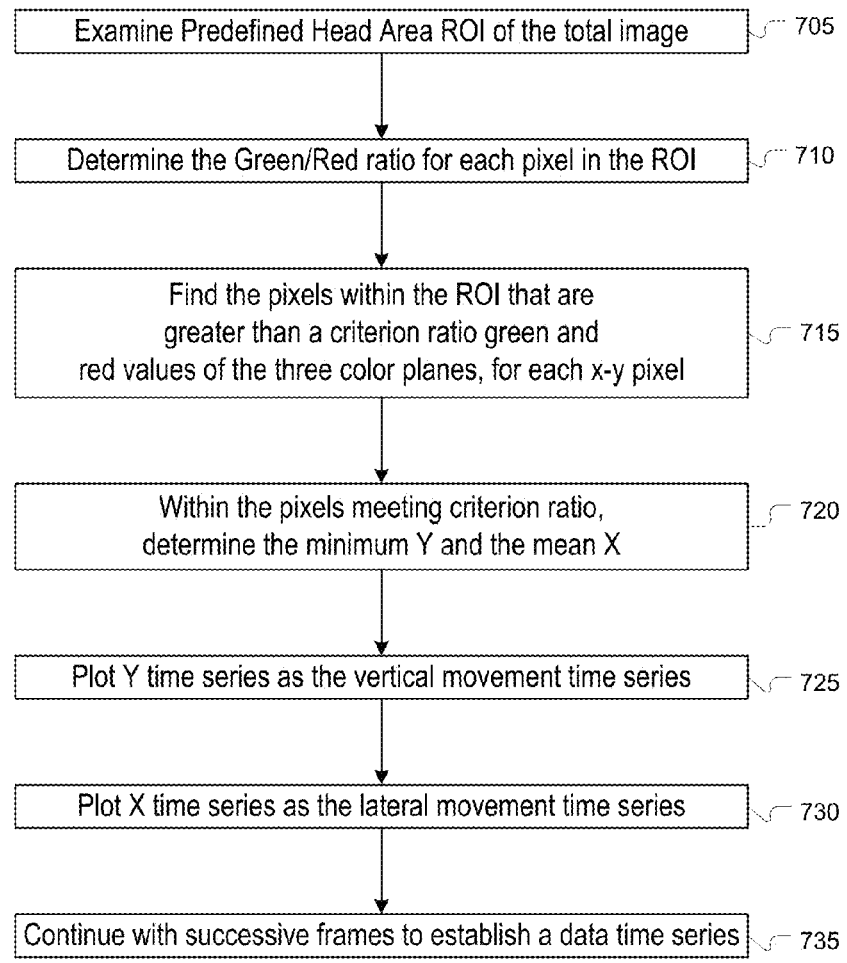
FIG. 7 shows a flowchart for a head movement measuring method for comprehensive human movement analysis according to one embodiment.

FIG. 7 shows a flowchart for a head movement measuring method for comprehensive human movement analysis according to one embodiment. Head Measuring Process 700 is used either when the subject or patient is standing in place, or transitioning from a sitting position to a standing position in order to measure vertical and lateral head movement, such as postural sway. The process 700 has the following steps: in step 705, the predefined head area ROI (Region of Interest) is examined preferentially, placing preference on the ROI out of the total image. In step 710, the green/red ratio for each pixel in the ROI is determined. In step 715, the process finds the pixels within the ROI that are greater than a criterion ratio of green and red values of the three color planes, for each x-y pixel. Then, in step 720, within the pixels meeting the criterion ratio of green and red values, the process determines the minimum Y value and the mean X value. In step 725, the process plots the Y time series as a vertical movement time series. In step 730, the process plots the X time series as a lateral movement time series. In step 735, the process is continued with successive frames of the ROI in order to establish a data time series. The end-result of the data time series can be used in subsequent analysis processing, such as the procedures discussed in FIGS. 3 and 4A-4B for the generation of form reports and plots. In the head area of a human patient there may be insufficient movement as to create a problem with the moment-to-moment variations in lighting of the hair, face and head in the room and lighting and patient placement of the present disclosure, so the detection and tracking of the object in the defined room setting and lighting is more reliable than in ambient settings and permits a more accurate measurement of head movement in a rising, side-to-side or front-to-back sway.

Gait or Walk Measuring

Figure 8:
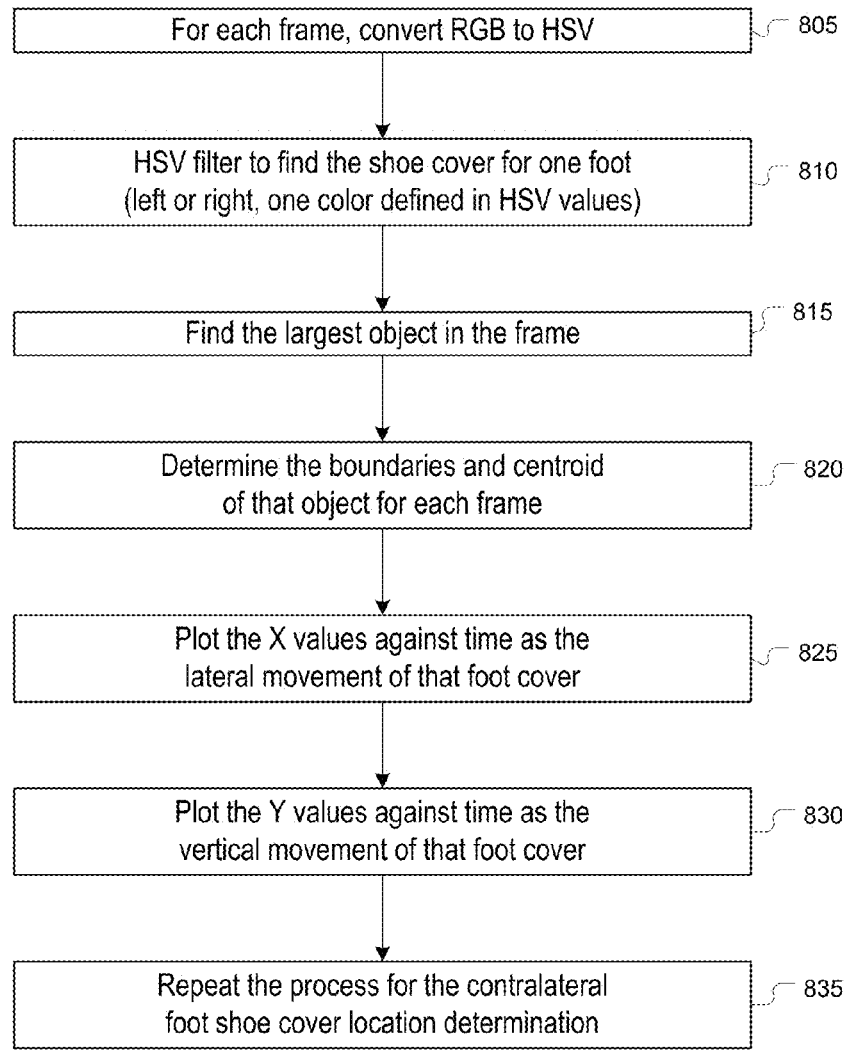
FIG. 8 shows a flowchart for a gait or walking measuring method for comprehensive human movement analysis according to one embodiment.

FIG. 8 shows a flowchart for a gait or walking measuring method for comprehensive human movement analysis according to one embodiment. Walk Measuring Process 800 is used to measure the gait of a subject or patient, where the subject is asked to walk from one side to another of the video stage area (the subject area 101 as detailed in FIG. 1A), where their line of walking motion is perpendicular to the view of the camera lens. Two distinctly colored shoe covers 90 (e.g., red and blue) are used in this above process.

The Walk Measuring Process 800 is able to measure the movement of each foot individually from a video sequence of frames. Process 800 has the following steps: in step 805, for each frame image in a video, the entire frame image is converted from RGB to HSV. In step 810, the converted image is run through an HSV filter in order to find the shoe cover 90 for one foot (left or right, the one color defined by the HSV filter parameter values). In step 815, the largest object in the frame is found. In step 820, the boundaries and centroid of that object (the largest object found in step 815) are determined for each frame image. In one embodiment, the boundaries and centroid approach is also applied to the head-measuring, finger-tapping and foot-tapping modules discussed above. In step 825, the process plots the X values against time as the lateral movement of a selected foot cover (repeated again for the other foot cover later). In step 830, the process plots the Y values against time as the vertical movement of a selected foot cover (repeated again for the other foot cover separately). Finally, in step 835, the process is repeated for the contralateral, or other foot shoe cover 90, in order to complete the location determination analysis. The end-result of the analysis (usually summarized in time series form) can be used in subsequent analysis processing, such as the procedures discussed in FIGS. 3A-3B and 4A-4B for the generation of form reports and plots. In one embodiment, the patient may walk to the camera and may be instructed to take five steps towards the camera, turn around and walk back to the chair, and then stand facing the chair. During the view of the camera from above the floor and 18 feet, for example, from the start point, the camera may be tilted down to view the legs and feet mostly. Due to the parallax and camera tilt, the view may be trapezoidal. By using a transform algorithm, which may be known in the art, the present disclosure may be able to track the foot prints as though they were on a flat, completely square checkerboard surface.

SALCP Algorithm

Figure 9:
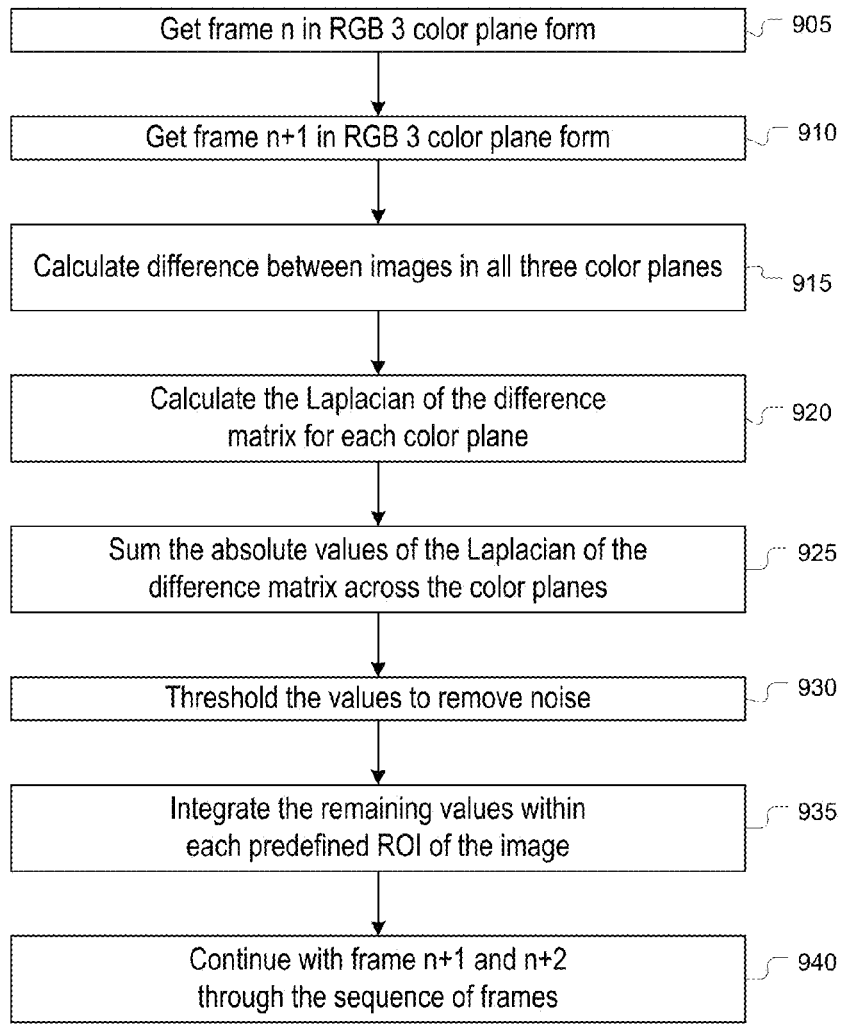
FIG. 9 shows a flowchart for a SALCP algorithm method used for the measure of spontaneous movements or tremors and used for comprehensive human movement analysis according to one embodiment.

FIG. 9 shows a flowchart for a SALCP method and algorithm method used for the measure of spontaneous movements or tremors and used for comprehensive human movement analysis according to one embodiment. SALCP effectively stands for a method and algorithm that takes the Summation of the Absolute Value of Laplacian transforms across all three Color Planes, wherein absolute values need not always be used but signed real number values or arithmetic values can be used as well. In one embodiment, the SALCP algorithm may be used for the measurement of spontaneous movements or tremors in the head, either or both hands or in either or both feet in the patient. It is a unique method and algorithm created by the inventor to be used for the present disclosure, but it may have a variety of other wide-ranging applications beyond comprehensive human movement analysis, such as applications in the video image processing and movement analysis fields. In the context of comprehensive movement analysis and this particular application, the SALCP method and algorithm can be used to measure spontaneous movement or tremors. It can be used alone, or combined with any of the other above described modules as a sub-process in a larger process or method and algorithm (e.g., Foot and Heel Tapping, Finger Tapping and Hand Flapping, Head Movement, Side View Walking, and/or additional types of analysis modules such as a subject/patient Sitting Quietly, Sitting and Talking, Going from Sitting to Standing, Standing in Place, and so on and so forth).

In one embodiment, the Laplace transform or Laplacian used in the SALCP algorithm discussed above may be computed in each instance for the region of interest in the color-containing difference between two individual frames of the video sequence recorded in the defined scene of a specific examination module. The Laplacian may be calculated for each pixel in each of the color plane difference matrices and that pixel's neighboring pixels in each individual color plane in a RGB or other plane representation scheme (e.g., RGB, HSV). The Laplacian of the pixel of a color plane relates the individual pixel to the difference from the average among its four neighbors. The Laplacian can be calculated using the relationship to the nearest neighbor(s) (i.e., in which the neighbor distance is one) or the relationship to other neighbors of a defined distance greater than one pixel (i.e., distance of two, three, or more pixels in each direction from the index pixel in each calculation). The result may then be converted to an absolute value for each such calculation for each of the color planes in the calculations related to the individual index pixel, and the process may be repeated throughout the pixels that represent the individual or plurality of pixels in the region of interest. The sum of the absolute values of the Laplacian of the individual color planes for each individual pixel location related to its neighbors (distance of n=1 or more) may be for the singular or plurality of pixels in the region of interest for that frame. The resulting matrix of SALCP values for the entire region of interest can then be filtered or "thresholded" to remove noise. The resulting net value matrix for the individual video frame may then be examined to determine the morphological objects in the frame and the boundaries, the leading and following relationships relative to the data from within the matrix for the individual frame and also relative to the data in the matrix derived from the prior video frame(s). Furthermore, centroid, orientation angle, corners, mid-lateral, mid-top and mid-bottom point coordinates for each object in the region of interest are taken as summary data by methods well known in the art, as well, for the derived data for the individual video frame. Upon completion of the SALCP derivations and summary data and coordinates for each object in each frame over the time of the full sequence of the frames, it is then possible to determine the net movement, relative movement rates, orientation of the object or objects in the frame, and across the frame sequences.

In one embodiment, a method and algorithm is disclosed using the Laplacian transform of each color plane of each individual video frame undergoing analysis for movement. The initial calculation registers the color representation matrices for one frame of a video image, the index frame, then subtracts the color representation matrices from a previous frame. The resulting difference matrices for the subtraction relative to the index frame are then subjected to the Laplace transform. The Laplace transforms for each of the color representation matrices (plane) produce Laplacian values, that may or may not be converted to absolute values, for each pixel space in each color plane in the difference matrices. Summation of the values or absolute values for a particular pixel position across each of the color representation planes using the Laplacian transforms of difference matrices produces a matrix of summed values that is the size of the original frame image or region(s) of interest in the index frame. The algorithm can be applied to a number of color representation conventions, including the RGB conventions, the ARGB and AYCoCg conventions, the various HSV conventions, the CIE-XYZ conventions, Y'UV conventions (including YUV420p and YUV422p and YCbCr), CMY(K) conventions, YIQ conventions, $VD_BD_R$ conventions, and YPBPR conventions. The values in the algorithm result in a matrix that represents color change values. These color change values can indicate change of color within an object in the field of view, or that are consistent with movement of an object or objects within the index frame relative to a prior frame in a background that is unchanging or changing at a different rate than the object of interest.

The Summation of the Absolute value of the Laplacian transform of the difference between Color-representation Planes of two successive (sequential or not sequential) video frames is the crux of the SALCP algorithm. The application of this algorithm can have relevance to many uses in color video frame analysis and is not intended in the present disclosure to be restricted to video recording analysis applications for human movement analysis. In one embodiment, this algorithm can be applied to analysis of live video in real time, or to post hoc analysis of video records to determine movement or relative rates of movement of an object or objects, or to determine local areas of color change with the field of view represented in the index video frame relative to the prior or successive differencing video frame for monitoring changes within or between objects in the field of view across time. The SALCP algorithm can be applied to interlaced as well as progressive scan video frame data conventions.

SALCP process 900 has the following steps: in step 905, the process gets frame "n" (an individual frame image from a sequence of frames making up a video file, wherein n is the subtractive frame), which is in a RGB 3-color plane form. In step 910, the process gets frame "n+i", the reference frame, where i is the size of frame difference (e.g., i=1 is the reference frame one frame different from the subtractive frame, i=2 is two frames removed from the subtractive frame, etc.). Also in step 910, the process may get frame "n+i" in RGB 3-color plane form. In step 915, the process calculates the difference between the images in terms of all three color planes resulting in a difference matrix for each of the three color representation planes. In step 920, the process then calculates the Laplacian (or Laplacian transform) of the difference matrix (found in steps 910-915) for each color plane. In step 925, the process sums the absolute values of the Laplacian of the difference matrix values across the color planes. In step 930, the values are put through a threshold in order to remove background noise. In step 935, the process integrates the remaining values within each predefined ROI of the image. Finally, in step 940, the process continues with frame n+1 and n+2 until all the frames in the sequence of frames are exhausted from the video. Again, the end-result of the SALCP method and algorithm analysis at step 940, for example, can be fed into other algorithms or analysis modules, can be entered into a time series data format, or can be ultimately used in subsequent analysis processing, such as the procedures discussed in FIGS. 3A-3B and 4A-4B for the generation of form reports and plots. In one embodiment, the present disclosure allows usage for analysis of the human movement examination modules and the audio and video recording of data for: Hand Alternating Supination-Pronation, Postural Tremor of Hands or Arms, Postural Instability and other overflow movements. In one embodiment, overflow movements may be specified that are not part of the instructed movement, but that spontaneously occur in some movement disorders in another limb or head of the same individual. While some movement may be passive, "en masse" movement, other movement may arise from spontaneous tremors in the hand or foot or head that is not performing the instructed movement for the examination item and module. Spontaneous tremors may also occur in the hand or foot that is performing the instructed movement examination item. The SALCP method and algorithm has particular utility in detecting and measuring these above-described types of movements.

In the flow charts, there is a "yes-no" dichotomizing in that the same process can be completed for different feet and/or hands. The operator ensures that the patient or subject has performed adequately in the video files presented for analysis. The unacceptable video files (erroneous or abortive attempts to perform) are stored in a subfolder and are not subject to analysis, only visual inspection. As such, it is necessarily true that the object in the video is in the proper position and in the lighting. Therefore, there are only decision points if the same algorithm is used to process right and left hand or foot performance, for example, such that the decision (dichotomy yes-no) is between the video file being of a left or right hand or foot performance, that is designated in the file name for automatic detection. However, automatic algorithm selection based upon filename read is trivial and not an aspect of the above application.

Therefore, the flowcharts are primarily "straight-through processing." This would be different if we were trying to pick out a person or movement within a scene that was not strictly defined. There is that capability, but one of the purposes of the above application is to measure neurologically relevant movements and vocal production(s) from a subject that is exhibiting standardized movement disorders known in neurology, where the scene and position and lighting are predefined in a room environment, as shown in the above application. Neurologically relevant types of movement from subjects, patients, objects, sound productions or vocal products from a subject, patient or object often exhibit standard or disordered movements known in the field of examination (such as neurology, orthopedics, physical therapy, occupational therapy, psychology, engineering, research), where the scene and position and lighting are predefined in a room environment. Object eccentric points and orientation angles permit the determination of the optimal position of an object (heads, hands, fingers, or other body parts or object parts, for example), and at that point, trimming of the pre-defined extraneous portions of the object is possible to eliminate a portion of the body part in the scene or another object within the image that is extraneous to the desired movement information focus in the analysis of a specific module recording data. For example, the forearm may be extraneous during the hand agility analysis, or another such object within the image, or the dim face of a patient—which is sometimes seen at the upper left hand or upper right hand border area of the finger tapping or hand flapping video frames.

Additional Modules
Postural Tremor of the Hands or Arms

Postural tremor of the hands or arms has been a standard part of clinical movement examination. The examination procedure instructs the patient to hold both hands straight out from the body, arms extended, for a period of several seconds. The examination measure variable is the presence (and severity and laterality) or absence of tremor in the extended hands-arms. Another examination variable is asymmetry of the posture of hands. In one embodiment, the patient is instructed by prerecorded audio instructions in the language of preference to extend the arms and hands forward at chest height, and to hold them in place until the instructions announce "Stop".

For recording postural tremor, video is recorded for several seconds at 30 or more frames per second. Tremor in the form of hand movement is measured using the morphological operations known in the art, or the SALCP protocol in each individual frame difference computed matrix, as the sum of the absolute values of the Laplacian of the difference between frames within each of the color planes. The thresholded value within each such difference matrix, in successive frames in the video sequence is examined within regions of interest that contain one or both of the hands. The "object" of the moving hand is detected by thresholding to indicate the "object" moving. The moving object is then characterized by its geometric characteristics: x-y coordinates relative to the frame of reference, for boundary locations, centroid, angle of orientation relative to the frame of reference, known in the art. These values are then collected as structures that contain the data for each leading frame relative to its differencing frame (n+i−n, where i=1 or i>1, etc). In this manner, the analysis of the sequential frames in the recorded video frame set is conducted for the full set of differenced frame pairs. Analysis of the movement of specific landmarks for one hand over the sampling rate may be done at 30 frames per second or greater. There may be no latency period in this item. There may be no "markers" used in this item.

Hand Alternating Supination-Pronation

Alternating supination-pronation of the hands has been a long-standing part of the clinical movement examination protocol. The examination procedure instructs the patient to hold both hands straight out from the body, arms extended, and to place both palms facing down, then axially rotate the hands at the wrist to palms facing up, and back to palms facing down. The alternating hand palms facing up and facing down (pronation and supination) is performed repeatedly and sequentially for an instructed minimum number of excursions or more. In one embodiment, the patient is instructed by prerecorded audio instructions in the language of preference to extend the arms and hands forward at chest height and to start with palms up, then palms down, then palms up and palms down, repeating the sequence for an instructed minimum number of excursions, until the prerecorded instructions announce "Stop".

Video may be recorded for a pre-specified duration. Hand pronation and supination movement is determined by the same method used in a postural tremor examination module, and the position of the boundaries of each hand is calculated as an X-Y movement data matrix, resulting in a movement data matrix for each hand individually. Correlation calculations between time series data for the two hand movement vectors provides a measure of the coordination between the two hands.

In each case, the background specular noise is used as the threshold above which movement (change in color in the space of the Cartesian position of the hand object from frame to frame) is developed as a calculated object.

Vectors are established for the X coordinates across the number of frames, and separately for Y coordinates across the frames.

There is a latency period in the hand supination-pronation performance recording, that is built into the audio instructions presentation file and the computer-timed delay to start recording, such that the patient/subject starts after the video-audio recording has begun, and the command "Start" is given after a fixed delay. In this manner, the absolute latency can be measured in the audio and video recording data between the end of the word "Start" in the audio instruction and the time of the first purposeful movement to start performing the instructed item.

Finger to Nose Movement Examination Module

Finger-To-Nose is the name of a long-standing clinical motor examination item that is clinically known. It is used routinely by physicians in neurological examination, even when not using formal movement observational rating scales. The examination procedure instructs the patient to place the index finger of one hand on the tip of the nose, then reach out to touch the extended index finger of the examiner, then back to the nose tip, and repeating these excursions for a total of an instructed minimum number of times, or a maximum time limit. In one embodiment, the procedure provides hand cast 80, a fixed cast of a human hand, that is positioned at a fixed distance relationship to the chair 10 in which the patient is sitting. In one embodiment, video recording begins before the auditory vocal signal command "Start", thereby establishing a latency period prior to the first performed excursion. Recording continues for a pre-specified period of time. One examination measure variable is the presence (and severity and laterality) or absence of tremor in the extended hands-arms during the excursions from nose to hand cast finger and hand cast finger to nose. Another examination variable is the accurate touching of the hand cast finger and the accurate touching of the person's own nose (e.g., the "targets"). The terms "hand cast" and "cast hand" are used interchangeably. The examination is then repeated independently, with the opposite hand, producing two records, one for performance with each hand. In this examination item, the procedure of the operator holding the operator's hand and finger for the patient to touch provides an inconsistent and variable target that does not permit standardized spatial parameters for quantitative analysis, nor for automated analysis of the movement instructed.

In one embodiment, a hand cast of a hand pointing its index finger up in the air is made of a soft, supple material that feels like human skin, and that is inert biologically inert and tolerates repeated cleaning for patient safety. The hand-cast 80 is mounted to a hand-cast mounting unit 81 on top of a post that rests on the floor at a fixed height relative to the patient, and mounts by a bar perpendicular to the post that ends in a hand-cast chair mounting unit 82 that attaches to the right or left cantilevered arms 11 of the chair 10. The chair 10 for the patient is modified to allow the patient to sit facing sideways, perpendicular to facing straight forward, in either direction, with a structurally supported chair arm still in place. In this embodiment, the chair 10 is equipped with stainless steel under-carriage cantilevering in the form of support arch 14 under each of the cantilevered chair arms 11 so that there are no impediments to movement of the patient's legs to the full right or full left position in the chair, while the arm remains structurally completely supportive. In this manner the patient can face directly toward the finger and hand that is presented as a target at either the right or the left side of the chair. This hand-plate-pole-mount assembly can be mounted and dis-mounted by the examiner with ease, and can be equivalently mounted at a standardized distance between the patient and the target hand and finger. The patient can adjust the position of the body in the chair to ensure that the distance from the target finger to the nose tip is within the arm's length of the patient without displacing the patient's body to complete each excursion. In one embodiment, the patient is instructed by prerecorded audio instructions in the language of preference to place the patient's designated hand (left or right) index finger tip on the patient's nose tip, then, when given the audio signal "Start", is asked to extend the arms and hand and index finger out to touch the target finger of the hand cast, then move the patient's arm and finger back to the patient's nose, repeating these excursions for an instructed number of excursions or continuing the repetitions for a fixed duration of video recording until audio instructions give the signal "Stop".

Video may be recorded for a pre-specified duration. Instructed excursions from nose tip to target finger and back are analyzed using the Laplacian frame analysis differencing method, for example, SALCP method 900. The hand agility analysis method (600) may also be used for the analysis of Finger-to-Nose recorded data. Tremor in hand movement is measured using the SALCP protocol in each individual frame difference computed matrix. The thresholded values within each such difference matrix, in successive frames in the video sequence is examined within regions of interest that contain one of the hands. The "object" of the moving hand is detected by thresholding to indicate the "object" moving. The moving object is characterized by its geometric characteristics: x-y coordinates relative to the frame of reference, for boundaries of eccentric points of the center-most largest object (e.g., the patient hand), for example, for eccentric points, boundaries, centroid, angle of orientation relative to the frame of reference. The distances between the fixed nose tip and the fixed hand cast index finder tip are calculated for each frame of data. These values are then collected as structures that contain the data for each leading frame relative to its differencing frame (n+1−n, where i=1 or i>1, etc.). In this manner, the analysis of the sequential frames in the video frame set is conducted for the plurality of frames difference data. Analysis of the movement of specific landmarks for one hand over the sampling rate of 30-60 frames per second or greater is fully accommodated in this embodiment. Resulting data is utilized in the steps consistent with the last steps outlined in FIGS. 4A and 4B.

There may be a latency period setting constructed in the module for this item. In one embodiment, the audio instruction presents the audio instruction of what movement to do and how often. Then the video and audio recording starts, followed by a fixed delay until the command "Start" is presented in the audio instruction. The subject/patient is to continue repeating the performance until this examination item movement is performed and recorded in complete detail for the left and for the right hands, separately, as two separate audio-video records.

The SALCP algorithm produces a thresholded net "image" object or objects in the region of interest that corresponds to each of the sequential video frames, then the coordinates of the object(s) are used to produce time series vectors of x, y coordinates of point or points on that image, centroid, angle of orientation, etc. Nose tip, patient/subject hand moving, and fixed position hand cast target are evident in the analysis as three distinct objects. The system is sensitive to touches on the nose, and touches on the index finger tip of the hand cast thereby permitting detection of accurate "strikes" or misses of each of the two spatially opposing targets.

Postural Instability

"Postural instability" is a standard item in neurological examination that has been a standard part of movement examination for years. The positioning of the patient relative to the wall, and the video analyses conducted to discern patient movement without contamination from operator movement is unique to this embodiment. The examination item instructs the patient to stand facing away from the examiner and in a pre-defined location in the room and video scene. The examiner approaches the patient from behind, and the patient is instructed that the examiner will pull backward a specified number of times at the patient's shoulders, and the patient is to try to remain standing in place. At intervals of a few seconds each, the examiner pulls back and down on both of the patient's shoulders. Notice is made of the tendency for the patient to fall, whether or not steps are taken backward to maintain standing upright position, and the length of time for the patient to resume an erect standing still position. In the current embodiment, the operator stands behind the patient, and the patient is at a pre-specified point in the room. In this manner, the patient is always at the operator's and camera's right most view region of the two objects in the overall scene.

The audio instructions contain soft "beep" sounds at fixed time intervals, that are the signal for the operator to effect the "pull" of both of the patient's shoulders. The analysis algorithms measure the complete excursions of the movement of the head of the patient and the movement of the feet in the patient. The analysis algorithms make use of the head finding method 700 and of the foot agility analysis method 500. The resulting measures can be located in specific time points and durations and latencies because the timing is always linked directly to the presentation latency for the signal to pull the shoulders, that are fixed in the sequence. Direct examination of the video and audio in the recorded sequences allows the determination of any delay on the part of the operator relative to the signals to pull. In this manner, the video analysis data for the movement of the head boundary, the excursion of that movement until it returns to a fixed steady standing erect position can be measured in a time resolution that is limited by the frame rate of the video recording. In most instances, the frame rate is sufficient to provide good resolution for the movement of the patient after each backward pull. All movements, durations, latencies of head and foot movements in the instances of backward pull for the session are then available as quantitative data from which to compare to normative values for intact persons performing the same test.

In one embodiment, the all of the steps of the methods described herein may be performed by one or more computers, including the computer 112. In one embodiment, some of the steps of the methods described herein may be performed by one or more computers, including the computer 112. In one embodiment, some of the steps of the methods described herein may be performed by an operator.

Figure 10:
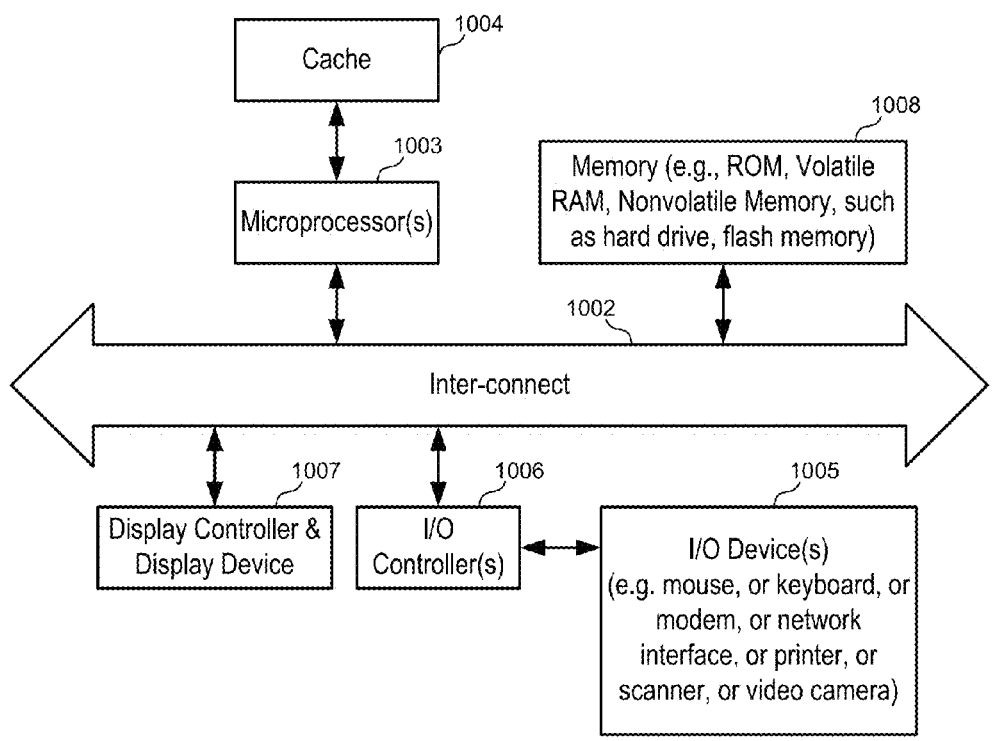
FIG. 10 shows a data processing system, according to one embodiment.

FIG. 10 shows a data processing system, which can be used in various embodiments. While FIG. 10 illustrates various components of a computer system, it is not intended to represent any particular architecture or manner of interconnecting the components. Some embodiments may use other systems that have fewer or more components than those shown in FIG. 10.

In one embodiment, the comprehensive human movement analysis system (e.g., 100, 120, 200) can be implemented as a data processing system, with fewer or more components, as illustrated in FIG. 10. When one or more components of the comprehensive human movement analysis system are implemented on one or more remote servers, the servers can be implemented as a data processing system, with fewer or more components, as illustrated in FIG. 10.

In FIG. 10, the data processing system 1000 includes an inter-connect 1002 (e.g., bus and system core logic), which interconnects a microprocessor(s) 1003 and memory 1008. The microprocessor(s) 1003 is coupled to cache memory 1004 in the example of FIG. 10.

The inter-connect 1002 interconnects the microprocessor(s) 1003 and the memory 1008 together and also interconnects them to a display controller, display device 1007, and to peripheral devices such as input/output (I/O) devices 1005 through an I/O controller(s) 1006.

Typical I/O devices include mice, keyboards, modems, network interfaces, printers, scanners, video cameras, audio mixer equalizers, audio output devices, signal lights, remote controls, remote control receivers, pan-tilt units, pan-tilt controllers, and other devices which are well known in the art. In some embodiments, when the data processing system is a server system, some of the I/O devices, such as printer, scanner, mice, and/or keyboards, are optional. Network interfaces or devices may also be provided to facilitate online access for repair and file upload.

The inter-connect 1002 may include one or more buses connected to one another through various bridges, controllers and/or adapters. In one embodiment, the I/O controller(s) 1006 includes a USB (Universal Serial Bus) adapter for controlling USB peripherals, and/or an IEEE-1394 bus adapter for controlling IEEE-1394 peripherals (and all other 1394-based systems), Gigawire, Bluetooth, Zigbee and IEEE 802.xxx interfaces.

The memory 1008 may include ROM (Read Only Memory), volatile RAM (Random Access Memory), and non-volatile memory, such as hard drive, flash memory, etc.

In the foregoing specification and the following appended documents, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

In this description, various functions and operations may be described as being, or are, performed by or caused by software code to simplify description. However, those skilled in the art will recognize that what is meant by such expressions is that the functions result from execution of the code/instructions by a processor, such as a microprocessor. Alternatively, or in combination, the functions and operations can be implemented using special purpose circuitry, with or without software instructions, such as using Application-Specific Integrated Circuit (ASIC) or Field-Programmable Gate Array (FPGA). Embodiments can be implemented using hardwired circuitry without software instructions, or in combination with software instructions. Thus, the techniques are limited neither to any specific combination of hardware circuitry and software, nor to any particular source for the instructions executed by the data processing system.

While some embodiments can be implemented in fully functioning computers and computer systems, various embodiments are capable of being distributed as a computing product in a variety of forms and are capable of being applied regardless of the particular type of machine or computer-readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

Routines executed to implement the embodiments may be implemented as part of an operating system or a specific application, component, program, object, module or sequence of instructions referred to as "computer programs". The computer programs typically include one or more instructions set at various times in various memory and storage devices in a computer, and that, when read and executed by one or more processors in a computer, cause the computer to perform operations to execute elements involving the various aspects.

A machine readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer to peer networks. Different portions of the data and instructions can be obtained from different centralized servers and/or peer to peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not necessary that the data and instructions be on a machine readable medium in entirety at a particular instance of time.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks (DVDs), Solid State Memory Devices (SSD), etc.), among others.

The computer-readable media may store the instructions. In general, a tangible machine-readable medium includes any mechanism that provides (i.e., stores and/or transmits) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

Although some of the drawings illustrate a number of operations in a particular order, operations which are not order dependent may be reordered and other operations may be combined or broken out. While some reordering or other groupings are specifically mentioned, others will be apparent to those of ordinary skill in the art and so do not present an exhaustive list of alternatives. Moreover, it should be recognized that the stages could be implemented in hardware, firmware, software or any combination thereof.

The disclosure includes methods and apparatuses which perform these methods, including data processing systems which perform these methods, and computer-readable media containing instructions which when executed on data processing systems cause the systems to perform these methods.

While the methods and systems have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

In this regard it should be understood that for practical reasons and so as to avoid adding potentially hundreds of claims, the applicant has presented claims with initial dependencies only.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive forms so as to afford the applicant the broadest coverage legally permissible in accordance with the following claims.

What is claimed is:

1. A non-transitory computer-readable medium having stored thereon a set of instructions, which when executed by a computer, perform a method, comprising:
    receiving module configuration settings to configure a customized human movement examination module for a human movement examination item;
    instructing a patient with audio instructions associated with the customized human movement examination module, wherein the audio instructions an instruction to begin action;

controlling a single camera having progressive scan capabilities according to the module configuration settings to allow recording of a performance by the patient of the human movement examination item;

identifying a specific body appendage of the patient in the recording;

analyzing the recording based on movement exhibited by the specific body appendage of the patient: and analyzing latency of the patient during the human movement examination item to respond to the instruction to begin action.

2. The computer-readable medium of claim 1, wherein the module configuration settings include at least one from a group consisting of camera zoom, camera focus, camera orientation, camera pan, camera frame rate, camera tilt, camera brightness, camera iris, camera gain, camera white balance blue, camera white balance red, and camera exposure.

3. The computer-readable medium of claim 1, wherein the module configuration settings include video and audio recording duration.

4. The computer-readable medium of claim 1, further comprising synchronizing the audio instructions with a recording delay and a recording duration.

5. The computer-readable medium of claim 1, wherein the analyzing further comprises:

applying a human movement analysis module technique to the recording consistent with the customized human movement examination module;

analyzing movement of the specific body appendage of the patient based on applying a tracking algorithm method to the recording consistent with the customized human movement examination module;

producing summary result data as a by-product of the module analysis technique; and comparing the summary result data to normative standards for the customized human movement analysis module to determine whether the patient exhibits a human movement disorder.

6. The computer-readable medium of claim 5, wherein the analyzing further comprises compiling the summary result data from multiple sessions of summary result data to perform overall analysis to measure whether the patient exhibits objective changes in the human movement disorder based on at least one of treatment, treatment change, medication maintenance, medication change, and the passage of time.

7. The computer-readable medium of claim 5, wherein the module analysis technique is a foot agility analysis wherein the patient wears colored shoe covers, the foot agility analysis comprising:

converting a frame image of the recorded foot movement data from RGB (Red Green Blue) to HSV (Hue Saturation and Value);

applying a HSV filter onto the converted HSV image;

converting the HSV filtered image into a binary image;

morphologically opening the binary image and finding the largest object in the morphologically opened image;

morphologically closing the image;

ascertaining the boundaries and coordinates of the largest object in the image and adding x-y coordinates of the boundaries into a time-series queue;

using photogrammetry calibration, calculating distance values of the boundaries and placing each calculated value into the time-series queue; and smoothing the data in the time-series queue for plotting, storage and output.

8. The computer-readable medium of claim 5, wherein the module analysis technique is a hand agility analysis comprising:

recording instructed hand movement of the patient;

deleting the green and blue color planes of each image frame from the recorded hand movement data to generate a red image;

converting the red image into binary form;

morphologically opening the binary image and finding the boundaries of the largest object in the image;

determining the angle of the largest object in the image;

rotating the largest object to an optimal position;

determining the eccentric points of the rotated largest object and ascertaining the angle of the eccentric points;

trimming the largest object by filling in extraneous areas of the largest object with black pixels;

determining the coordinates of the eccentric points of the trimmed largest object;

calculating the distances between eccentric points of the trimmed largest object;

adding the calculated distance values to a time series queue;

using calibration, converting the distance values in the time series queue into centimeters, wherein the calibration comprises photogrammetry calibration; and smoothing the data in the time-series queue for plotting, storage and output.

9. The computer-readable medium of claim 5, wherein the module analysis technique is a head movement analysis comprising:

determining the green/red ratio for each pixel in each frame of a recording of head movement data, wherein the recording is examined preferentially on a region of interest (ROI) where the head of the patient is most likely to be present;

finding the pixels within the frame that are greater than a criterion ratio of green and red values of the color planes for each x-y pixel;

within the pixels meeting the criterion ratio, determining the minimum y value and the mean x value;

plotting the y time series as a vertical movement time series;

plotting the x time series as a lateral movement time series;

continuing the process with successive frames of the recording of head movement data to establish a time-series queue combining both x and y time series data; and smoothing the data in the time-series queue for plotting, storage and output.

10. The computer-readable medium of claim 5, wherein the module analysis technique is a gait or walk measuring analysis, wherein the patient wears two distinctly colored shoe covers, one on each shoe, the gait or walk measuring analysis comprising:

recording the walk movement data as the patient walks from one extreme side of the area perceived by the single camera to the other extreme side of the area perceived by the single camera;

converting a frame image of the recorded walk movement data from RGB (Red Green Blue) to HSV (Hue Saturation and Value);

applying a HSV filter onto the converted HSV image;

converting the HSV filtered image into a binary image;

morphologically opening the binary image and finding the largest object in the morphologically opened image;

morphologically closing the image;

ascertaining the boundaries and centroid of the largest object in the image and adding coordinates of the boundaries and centroids into a time-series queue;

plotting the x values of coordinates of the ascertained boundaries against time as the lateral movement of a selected foot cover and repeating the plot for the other foot cover;

plotting the y values of coordinates of the ascertained boundaries against time as the vertical movement of a selected foot cover and repeating the plot for the other foot cover;

combining the plotted x and y data into a time-series queue; and smoothing the data in the time-series queue for plotting, storage and output.

11. The computer-readable medium of claim 5, wherein the module analysis technique is a finger-to-nose movement analysis comprising:

instructing the patient to touch the finger of an artificial hand-cast means with the patient's finger;

instructing the patient to bring the patient's finger back from the finger of the artificial hand-cast means to touch the patient's own nose repetitively;

recording the patient's hand movement with the single camera;

deleting the green and blue color planes, but keeping the red color plane, of each image frame from the recorded hand movement image data;

converting the red color plane image into binary form;

morphologically opening the binary image and finding the boundaries of the largest objects in the image, wherein the largest objects in the image comprise the artificial hand-cast means, the hand of the patient and the patient's head;

determining the orientation angle of the center-most of the largest objects in the image;

determining the eccentric points of the center-most of the largest objects and ascertaining the angle of the eccentric points of the center-most of the largest objects;

determining the coordinates of the eccentric points of the center-most largest objects;

calculating the distances between eccentric points of all the largest objects relative to each other;

adding the calculated distance values to a time series queue;

using calibration, converting the distance values in the time series queue into centimeters, wherein calibration comprises photogrammetry calibration;

smoothing the data in the time-series queue for plotting, storage and output; and summarizing the mean peak distance of the distance between the thumb and index finger or the distance between the fingertips and the palm of the hand of the patient.

12. The computer-readable medium of claim 11, wherein the artificial hand-cast means is made of elastomeric material and configured to simulate appearance of a human hand.

13. The computer-readable medium of claim 5, wherein the tracking algorithm is a Summation of the Absolute value of Laplacian transforms for all three Color Planes (SALCP) algorithm method.

14. The computer-readable medium of claim 13, wherein the SALCP algorithm method comprises:

taking frame "n" of the recording and keeping it in RGB 3-color plane form as the subtractive frame;

getting frame "n+i" of the recording as the reference frame, wherein i is the size of the frame number difference from the reference frame to the subtractive frame "n";

calculating the difference between frame "n" and all frames "n+i" in terms of each of the three color planes, for each (subtractive-frame, reference-frame) pair in the frames sequence, and creating a difference matrix for each color plane for each (subtractive-frame, reference-frame) pair;

calculating the Laplacian transform of the difference matrix for each color plane;

summing up the absolute value of the Laplacian transform of the difference matrix for each pixel cell across the color planes, resulting in a single matrix with the same number of cells and dimensions as the original pixels of the original reference video frame;

putting the values through a thresholding process in order to avoid background noise;

integrating the remaining values within each predefined region of interest (ROI) of the image; and continuing with frame "n+i" in the next i value until all the (reference frame, subtractive frame) pairs in the sequence of frames are exhausted from the recording.

15. A system comprising:

a single camera having progressive scan capabilities; and a computing device coupled to the single camera, wherein the computing device is configured to:

receive module configuration settings to configure a customized human movement examination module for a human movement examination item, instruct a patient with audio instructions associated with the customized human movement examination module, control the single camera according to the module configuration settings to allow recording of a performance by the patient of the human movement examination item, identify a specific body appendage of the patient in the recording, analyze the recording based on movement exhibited by the specific body appendage of the patient, and analyze latency of the patient during the human movement examination item to respond to an instruction to begin action, wherein the audio instructions include the instruction to begin action.

16. The system of claim 15, wherein the single camera is configured to communicatively couple the single camera to the computer device.

17. The system of claim 15, wherein the system further comprises:

computer storage to store data provided by the single camera, wherein the data comprises video and audio data;

pan-tilt unit to fix the single camera based on predetermined pan-tilt settings, associated with the customized human movement examination module, during the recording, wherein the pan-tilt unit is controlled by a pan-tilt control unit.

18. A method comprising:

receiving, via a computing device, module configuration settings to configure a customized human movement examination module for a human movement examination item;

instructing, via the computing device, a patient with audio instructions associated with the customized human movement examination module, wherein the instructions include an instruction to begin action;

controlling, via the computing device, a single camera having progressive scan capabilities according to the module configuration settings to allow recording of a performance by the patient of the human movement examination item;

identifying, via the computing device, a specific body appendage of the patient in the recording;

analyzing, via the computing device, the recording based on movement exhibited by the specific body appendage of the patient; and analyzing latency of the patient during the human movement examination item to respond to the instruction to begin action.

* * * * *